(12) United States Patent
Yuan et al.

(10) Patent No.: US 8,795,979 B2
(45) Date of Patent: Aug. 5, 2014

(54) HYDROLASE ENZYME SUBSTRATES AND USES THEREOF

(75) Inventors: Chong-Sheng Yuan, San Diego, CA (US); Xiaoru Chen, San Diego, CA (US)

(73) Assignee: General Atomics, San Diego, CA (US)

( * ) Notice: Subject to any disclaimer, the term of this patent is extended or adjusted under 35 U.S.C. 154(b) by 0 days.

(21) Appl. No.: 13/352,273

(22) Filed: Jan. 17, 2012

(65) Prior Publication Data

US 2012/0190013 A1 Jul. 26, 2012

Related U.S. Application Data

(60) Provisional application No. 61/433,909, filed on Jan. 18, 2011.

(51) Int. Cl.
*C12Q 1/34* (2006.01)
*C12Q 1/44* (2006.01)
*G01N 33/53* (2006.01)
*C07H 15/10* (2006.01)
*C07H 15/18* (2006.01)

(52) U.S. Cl.
CPC .............. *C07H 15/10* (2013.01); *C07H 15/18* (2013.01)
USPC .............. 435/18; 435/19; 435/6.1; 435/7.1; 536/4.1

(58) Field of Classification Search
USPC .......................... 435/18, 19, 6.1, 7.1; 536/4.1
See application file for complete search history.

(56) References Cited

U.S. PATENT DOCUMENTS

| | | | |
|---|---|---|---|
| 3,183,235 A | 5/1965 | Zenitz | |
| 3,275,680 A | 9/1966 | Holzrichter et al. | |
| 3,290,326 A | 12/1966 | Hoffer | |
| 4,020,070 A | 4/1977 | Gauri | |
| 4,111,751 A | 9/1978 | Lange, III et al. | |
| 4,131,727 A | 12/1978 | Lange, III et al. | |
| 4,241,184 A | 12/1980 | Hou et al. | |
| 4,544,638 A | 10/1985 | Siegel | |
| 4,619,898 A | 10/1986 | Hopkins | |
| 4,708,929 A | 11/1987 | Henderson | |
| 4,729,956 A | 3/1988 | Hopkins | |
| 4,956,290 A | 9/1990 | Harrison, Jr. et al. | |
| 4,963,539 A | 10/1990 | Deleaney | |
| 4,985,365 A * | 1/1991 | Mitsuda et al. | 435/280 |
| 5,120,653 A | 6/1992 | Henderson | |
| 5,156,955 A | 10/1992 | Isono et al. | |
| 5,162,203 A | 11/1992 | Vallee | |
| 5,162,516 A | 11/1992 | Ingram et al. | |
| 5,166,329 A | 11/1992 | Cregg | |
| 5,182,209 A | 1/1993 | Geerlof et al. | |
| 5,244,785 A | 9/1993 | Loor et al. | |
| 5,344,777 A | 9/1994 | Tamaki et al. | |
| 5,362,625 A | 11/1994 | Krevolin et al. | |
| 5,385,833 A | 1/1995 | Bradshaw et al. | |
| 5,445,943 A | 8/1995 | Hoenes | |
| 5,695,973 A | 12/1997 | Subbiah | |
| 5,855,881 A | 1/1999 | Loike et al. | |
| 5,906,930 A * | 5/1999 | Arnold et al. | 435/197 |
| 5,908,924 A | 6/1999 | Burdette et al. | |
| 6,225,099 B1 | 5/2001 | Hummel et al. | |
| 6,255,092 B1 | 7/2001 | Kojima et al. | |
| 6,262,295 B1 | 7/2001 | Bernegger et al. | |
| 6,432,688 B1 | 8/2002 | Ito et al. | |
| 6,552,249 B1 | 4/2003 | Cahoon et al. | |
| 6,710,200 B2 * | 3/2004 | Hammock et al. | 558/303 |
| 6,835,212 B2 | 12/2004 | Rozzell et al. | |
| 7,160,708 B2 | 1/2007 | Eirich et al. | |
| 7,354,751 B2 | 4/2008 | Nakano | |
| 7,750,135 B2 | 7/2010 | Zeikus et al. | |
| 2002/0187942 A1 | 12/2002 | Koguchi et al. | |
| 2006/0074060 A1 | 4/2006 | Vicker et al. | |
| 2009/0017510 A1 | 1/2009 | Gupta et al. | |
| 2009/0053780 A1 | 2/2009 | Hanke | |
| 2009/0186900 A1 | 7/2009 | Vicker et al. | |
| 2010/0063294 A1 | 3/2010 | Kuriyama et al. | |
| 2010/0093720 A1 | 4/2010 | Marsault et al. | |

FOREIGN PATENT DOCUMENTS

| | | |
|---|---|---|
| JP | 2147956 | 6/1990 |
| WO | WO-96/41172 | 12/1996 |
| WO | WO-2006/058940 | 6/2006 |
| WO | WO-2009/047311 | 4/2009 |
| WO | WO-2009/117728 | 9/2009 |

OTHER PUBLICATIONS

Parente et al., J. Am. Chem. Soc. 106, 8156-8161 (1984).*
Schray et al., "Mechanisms of Hydrolysis of Phosphate Ester Derivatives of Phosphoenolpyruvic Acid", Journal of the American Chemical Society (1971) 93(10):2522-2529.
Written Opinion for PCT/US12/21607, mailed Jan. 29, 2013.
Baldwin et al., "New Photolabile Phosphate Protecting Groups" Tetrahedron (1990) 46(19):6879-6884.
Guillen and Evans, "Anisaldehyde and Veratraldehyde Acting as Redox Cycling Agents for H2O2 Producation by *Pleurotus eryngii*" Appl. Environmental Microbiol. (1994) 60(8):2811-2817.
International Search Report for PCT/US2012/021607, mailed on May 25, 2012.

(Continued)

*Primary Examiner* — Chih-Min Kam
(74) *Attorney, Agent, or Firm* — Morrison & Foerster LLP

(57) ABSTRACT

The present invention provides novel methods for determining the presence or amount of a hydrolytic enzyme in a sample, based on novel substrates for the enzymes, and also provides compositions and methods that provide highly sensitive assay methods for such hydrolytic enzymes.

31 Claims, 12 Drawing Sheets

(56) References Cited

OTHER PUBLICATIONS

Kawahara et al., "Chemoenzymatic Synthesis of Sacranosides A and B" Chemical & Pharmaceutical Bulletin (2006) 54(3):387-390.
Reiser et al., "Aryl-alcohol Dehydrogenase from the White-rot Fungus *Phanerochaete chrysosporium*" Journal of Biological Chemistry (1994) 269(45):28152-28159.
Van Herk et al., "Regioselective phosphorylation of carbohydrates and various alcohols by bacterial acid phosphatases; probing the substrate specificity of the enzyme from *Shigella flexneri*" Advanced Synthesis & Catalysis (2005) 347(7):1155-1162.
Wood et al., "Base composition-independent hybridization in tetramethylammonium chloride: A method for oligonucleotide screening of highly complex gene libraries" PNAS USA (1985) 82:1585-1588.
Written Opinion of the International Searching Authority for PCT/US2012/021607, mailed on May 25, 2012.
International Preliminary Report on Patentability for PCT/US12/21607, mailed Jun. 17, 2013, 8 pages.
Broach et al., "High-throughput screening for drug discovery" Nature (1996) 384:14-16.
Burbaum et al., "New technologies for high-throughput screening" Curr. Opin. Chem. Biol. (1997) 1:72-78.
Farmer et al., "Aromatic-Alcohol-Oxidase Activity in the Growth Medium of Polystictus versicolor" Biochem. J. (1960) 74:257-262.
Fernandes, "Letter from the Society President" J. Biomol. Screening (1997) 2:1.
Guillen et al., "Substrate specificity and properties of the aryl-alcohol oxidase from the ligninolytic fungus *Pleurotus eryngii*" Eur. J. Biochem. (1992) 209:603-611.
Janssen and Ruelius, "Alcohol Oxidase, A Flavoprotein From Several Basidiomycetes Species" Biochim. Biophys. Acta. (1968) 151(2):330-342.
Janzen et al., "High Throughput Screening as a Discovery Tool in the Pharmaceutical Industry" Lab Robotics Automation (1996) 8261-8265.
Jenkins, "Homogenous enzyme immunoassay" J. Immunol. Meth. (1992) 150:91-97.
Patel and Nash, "Innovations in Non-Isotopic DNA Sequencing: Using an Electrotransfer Unit to Blot Sequencing Gels and an Automated Membrane Processor for Detecting DNA Sequences" Biotechniques (1995) 18(2):328-333.
Shaw et al., "Kinetic Studies on Benzyl Alcohol Dehydrogenase Encoded by TOL Plasmid pWW0" J. Biol. Chem. (1993) 268:10842-10850.
Suhara et al., "The Purification and Properties of Benzylalcohol Dehydrogenase from *Pseudomonas* Sp." Arch. Biochem. Biophys. (1969) 130:422-429.
Suye, "Purification and Properties of Alcohol Oxidase from *Candida methanosorbosa* M-2003" Curr. Microbiol. (1997) 34(6):374-377.
Wild, "Enzyme Labels" in The Immunoassay Handbook, $3^{rd}$ ed., Elsevier Press (2005), p. 194-95.
Yakushi and Matsushita, "Alcohol dehydrogenase of acetic acid bacteria: structure, mode of action, and applications in biotechnology" Appl. Microbiol. Biotechnol. (2010) 86(5):1257-65.
Yamanaka and Minoshima, "Identification and Characterization of a Nicotinamide Adenine Dinucleotide-Dependent p-Hydroxybenzyl Alcohol Dehydrogenase from *Rhodopseudomonas acidophila* M402" Agric. Biol. Chem. (1984) 48:1161-1171.
Yin, "Alcohol Dehydrogenase: Enzymology and Metabolism" Alcohol Alcohol. Suppl. (1994) 2:113-119.
Response to Written Opinion with Chapter II Demand and Article 34 Amendments, filed Nov. 16, 2012, 41 pages.

* cited by examiner

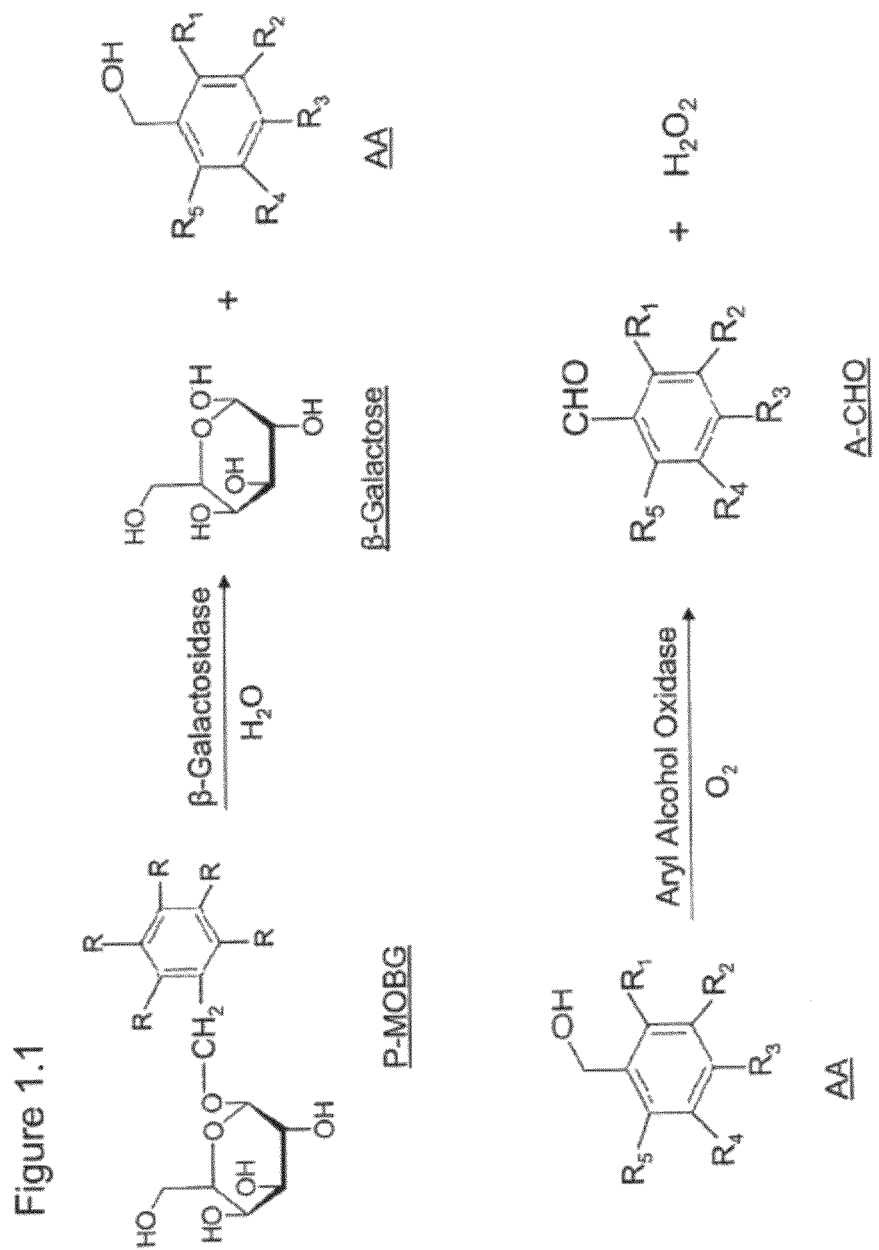
Figure 1.1

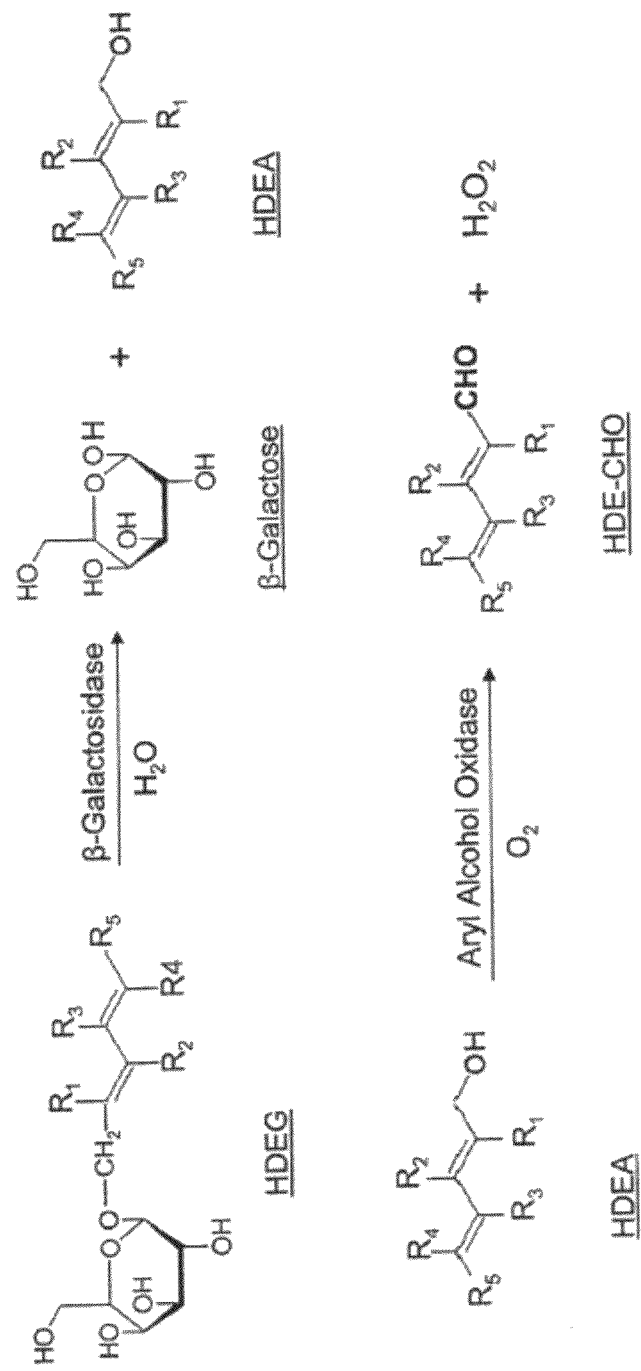

HYDROLASE ENZYME SUBSTRATES AND USES THEREOF

CROSS-REFERENCE TO RELATED APPLICATION

This application claims the priority benefit of U.S. provisional application Ser. No. 61/433,909, filed Jan. 18, 2011, the content of which is incorporated by reference in its entirety.

FIELD OF THE INVENTION

This invention generally relates to certain hydrolase enzyme substrates and uses thereof. In particular, the invention provides novel compounds that function as substrates for some hydrolytic enzymes, whereby the hydrolytic enzyme converts the hydrolase substrate into a hydrolysis product that can be readily detected, e.g., by enzymatic methods described herein.

BACKGROUND OF THE INVENTION

Enzymes have been widely utilized as sensitive labels in a number of biochemical systems, including immunoassays such as ELISA systems, and nucleic acid assays such as PCR and sequencing systems. The enzymes are often detected indirectly, based on their activity, typically based on their transformation of substrate into product, or of a co-factor between, e.g., oxidized and reduced states.

In some implementations, the enzyme to be detected is attached to a highly specific complexing or binding agent such as an antibody. When the antibody binds to a target molecule to be detected, the antibody complex can be detected by observing the presence of the enzyme label attached to it; the enzyme is readily detected based on its activity. In other systems, an oligonucleotide to be expressed is labeled by linking it to a nucleotide that encodes an enzyme that can function as a label. When the oligonucleotide is expressed, the protein product that includes the enzyme label, which facilitates detection, again based on the activity of the enzyme.

Detecting the activity of the enzyme provides very efficient signal amplification. Rather than detecting the often small amount of enzyme (or target compound) present, one looks for the activity of the enzyme, i.e., its effect on known substrates that can be added in relatively large amounts. A single enzyme molecule can catalyze transformation of a large number of substrate molecules (e.g., an enzyme may catalyze $10^7$ reactions per minute: *THE IMMUNOASSAY HANDBOOK*, $3^{rd}$ ed. by David Wild, Elsevier Press, pg. 194 (2005)), so the species actually detected can be a product formed by the enzyme or the disappearance of a substrate or co-factor consumed by the enzyme, instead of the enzyme itself. Thus when observing the enzyme's activity, one detects large numbers of substrate or product molecules rather than the enzyme itself, which provides a highly amplified signal.

A number of such enzyme labels are known: the ones most commonly used in immunoassays (e.g., ELISA) include horseradish peroxidase and alkaline phosphatase. Others that have been used include acetate kinase, firefly luciferase, xanthine oxidase, beta-D-galactosidase, glucose oxidase, and glucose 6-phosphate dehydrogenase. Id. at 194-195.

However, there remains a need for new methods to label biochemical species to facilitate detection of extremely small quantities, and novel enzyme labeling systems are thus needed. There also remains a need for methods to detect trace amounts of hydrolytic enzymes in other settings where they are not used just as labels. The present invention provides such methods as well as compounds and compositions for use in these methods and conditions.

BRIEF SUMMARY OF THE INVENTION

In one aspect, the present invention provides for substrates for certain hydrolytic enzymes, compositions containing these substrates, and methods to use these substrates to determine the presence of a hydrolytic enzyme that can process the substrates. In some embodiments, the hydrolytic enzyme may be used as a label for an assay system such as ELISA, for example, or a nucleic acid encoding the hydrolytic enzyme may be attached to an oligonucleotide to be expressed in such a way that expression of the oligonucleotide produces a polypeptide that includes the functional hydrolytic enzyme: the compositions and methods described herein are useful to detect the hydrolytic enzymes in these and other systems.

In one aspect, the invention provides for a compound of this formula, which is a substrate for a hydrolytic enzyme of interest:

(I)

wherein:
  A is an aromatic or heteroaromatic group, a 1-alkene or a 1-alkyne, each of which is optionally substituted;
  each R is independently H or an optionally substituted C1-C4 alkyl or C6-C10 aryl;
  n is an integer from 1-4;
  and X is a group comprising a substrate moiety,
    wherein the substrate moiety comprises a molecular fragment that is a substrate for the hydrolytic enzyme, and wherein the activity of the hydrolytic enzyme is capable of hydrolyzing the compound of formula (I) to form compounds (II) and (III):

(II)

(III)

In these compounds, A can be an aromatic or heteroaromatic group, e.g., a 5-6 membered aromatic ring optionally containing up to three heteroatoms selected from N, O and S as ring members; or a bicyclic ring system having 8-10 ring members, up to four of which can be heteroatoms selected from N, O and S. In some embodiments, A is phenyl or naphthyl. A can be optionally substituted as described herein, typically with up to three substituents selected from those described herein as suitable for aryl or heteroaryl groups.

In alternative embodiments, A is a 1-alkenyl or 1-alkynyl group, typically containing 2-10 carbon atoms and preferably 2-6 carbon atoms. In these embodiments, A can be substituted with the groups described herein as suitable for alkyl groups, to the extent valence permits such substitution. Typically, A is substituted with up to three substituents in these embodiments.

In specific embodiments of these compounds, n is 1. Because A is an aryl, heteroaryl, 1-alkene or 1-alkyne, when n is 1, the compounds are of the formula:

(IIB)

These embodiments are activated toward oxidation of the hydroxyl group shown, because the A group makes the alcohol in formula IIB a benzylic, allylic, propargylic, or similarly activated hydroxyl. These compounds are particularly suitable for oxidation by aryl alcohol oxidase, alcohol dehydrogenase, and/or aryl alcohol dehydrogenase enzymes. In some embodiments of these compounds, R is H, and the product of the oxidation is an aldehyde, e.g., the product will be a benzaldehyde when A is a phenyl moiety.

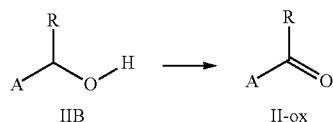

IIB    II-ox

These embodiments are also particularly well suited for use in a cycling system that amplifies the detectable signal and substantially increases sensitivity. The cycling system requires the presence of an additional enzyme that oxidizes the initial product of the hydrolysis reaction (the alcohol IIB shown above) to form an oxidized product of formula II-ox; and a reducing enzyme to reduce the oxidized product back to the alcohol IIB:

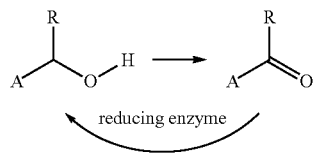

This produces a cycling system that can amplify the effective signal from the initial hydrolysis of the substrate of Formula I. The cycling can be conducted using any suitable reagents, such as the aryl alcohol oxidase and aryl alcohol dehydrogenase described in Guillen and Evans, *Appl. Environmental Microbiol.*, 60(8):2811-17 (1994). The cycling system can be used to detect a small amount or level of a hydrolytic enzyme of interest, e.g., at millimolar, micromolar, nanomolar, picomolar, femtomolar, attomolar or even sub-attomolar, e.g., zeptomolar or yoctomolar, level.

In the present system, the cyclic process increases the amount of an analyte that can be detected and correlated with enzymatic activity levels. Rather than detecting only the hydrolysis product formed by the direct action of the enzyme, which may already provide good sensitivity, one can detect instead a by-product from the cycling reaction that is produced in either the oxidation reaction or a subsequent reaction of the oxidized product (ketone or aldehyde) as the initial hydrolysis product is cycled between oxidized and reduced forms. The cycling reaction shown above can produce large amounts of such by-products, e.g., $H_2O_2$, produced in the oxidation reaction, or NAD+ or NADP+, produced in the reducing reaction. Additionally or alternatively, one can monitor disappearance of NADH or NADPH consumed in the reduction reaction that is involved when the cycling reaction system is operating. Because the amount of these detectable species can be much larger than the amount of the hydrolytic enzyme substrate due to the cycling reaction, sensitivity can be significantly increased by using such cycling methods.

In some embodiments, the oxidation is accomplished by an aryl alcohol oxidase using $O_2$ as the oxidant, and producing $H_2O_2$ as a by-product. This $H_2O_2$ can be detected to determine the presence or amount of hydrolytic enzyme in the reaction. Methods for determining $H_2O_2$ in small amounts are well known in the art. Reagents for measuring $H_2O_2$ include a peroxidase enzyme, an aminoantipyrine (e.g., 4-aminoantipyrine (4-AA)), a phenol, and/or an aniline analog. For example, the Trinder reaction can be used, requiring a phenol or aniline analog, a peroxidase such as horseradish peroxidase, and 4-AA. This method can be practiced without any need for the reducing enzyme or the cycling reaction.

In some embodiments, a reducing enzyme is included in the test milieu, typically a dehydrogenase (aryl alcohol dehydrogenase, alcohol dehydrogenase), and a reducing co-factor is included (e.g., NADH, NADPH), often in large excess. The co-factor is oxidized to form NAD+ or NADP+ during the cycling reaction, and the appearance of this oxidized form (NAD+ or NADP+) or the disappearance of the reduced form (NADH or NADPH) can be measured by methods well known in the art. Because the reaction mixture also contains an enzyme that oxidizes the alcohol of Formula (II) or (IIb), the result can be a cycling assay system as further described herein.

The various reagents and/or enzymes, include the hydrolytic enzymes, alcohol oxidase, aryl alcohol oxidase, alcohol dehydrogenase, and/or aryl alcohol dehydrogenase, can be provided and/or used in any suitable forms. In some embodiments, the various reagents and/or enzymes are provided and/or used in isolated forms. In other embodiments, the various reagents and/or enzymes are provided and/or used in a mixture.

A more detailed description of certain embodiments of the invention is provided below to illustrate its scope and operation.

BRIEF DESCRIPTION OF THE DRAWINGS

FIG. 1.1 illustrates the reaction of an enzyme substrate of the invention having a benzyl-substituted galactose, reacting with a beta-galactosidase to release a benzyl alcohol, which is then oxidized by aryl alcohol oxidase and oxygen to a benzaldehyde and hydrogen peroxide.

FIG. 1.2 illustrates an olefin-containing galactosidic enzyme substrate that is hydrolyzed by beta-galactosidase to release an allylic alcohol, followed by oxidation of the allylic alcohol to an aldehyde and hydrogen peroxide.

FIG. 9 further illustrates using a reductive enzyme (aryl alcohol dehydrogenase or alcohol dehydrogenase) to reduce the benzaldehyde, providing a cycling enzyme system. The reduction step regenerates the benzylic alcohol and produces an oxidized co-factor (NAD+ or NADP+), so the rate of consumption of reduced co-factor or the rate of formation of the oxidized co-factor can be monitored to measure the amount of alkaline phosphatase present. Alternatively or in addition, as shown in FIG. 8, a Trinder reaction can be used to measure the hydrogen peroxide produced to determine the amount of alkaline phosphatase present.

DETAILED DESCRIPTION OF THE INVENTION

Figure 2:
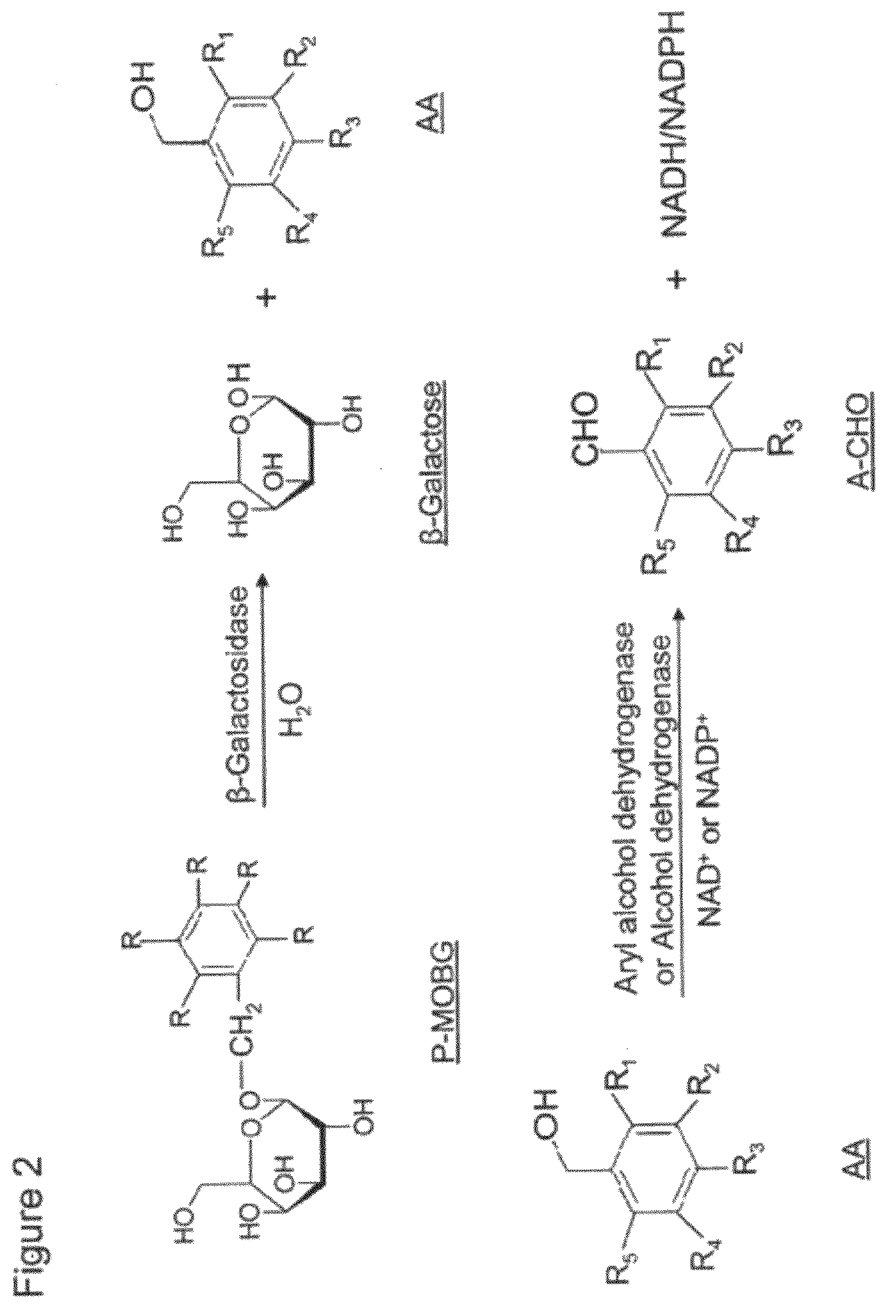
FIG. 2 illustrates a benzylic galactosidic enzyme substrate that is hydrolyzed by beta-galactosidase to form a benzylic alcohol, and subsequent oxidation of the benzylic alcohol by an additional enzyme (aryl alcohol dehydrogenase or alcohol dehydrogenase). The enzymatic oxidation uses a co-factor, NAD+ or NADP+, which gets reduced by the oxidation step to form NADH or NADPH.
Figure 3:
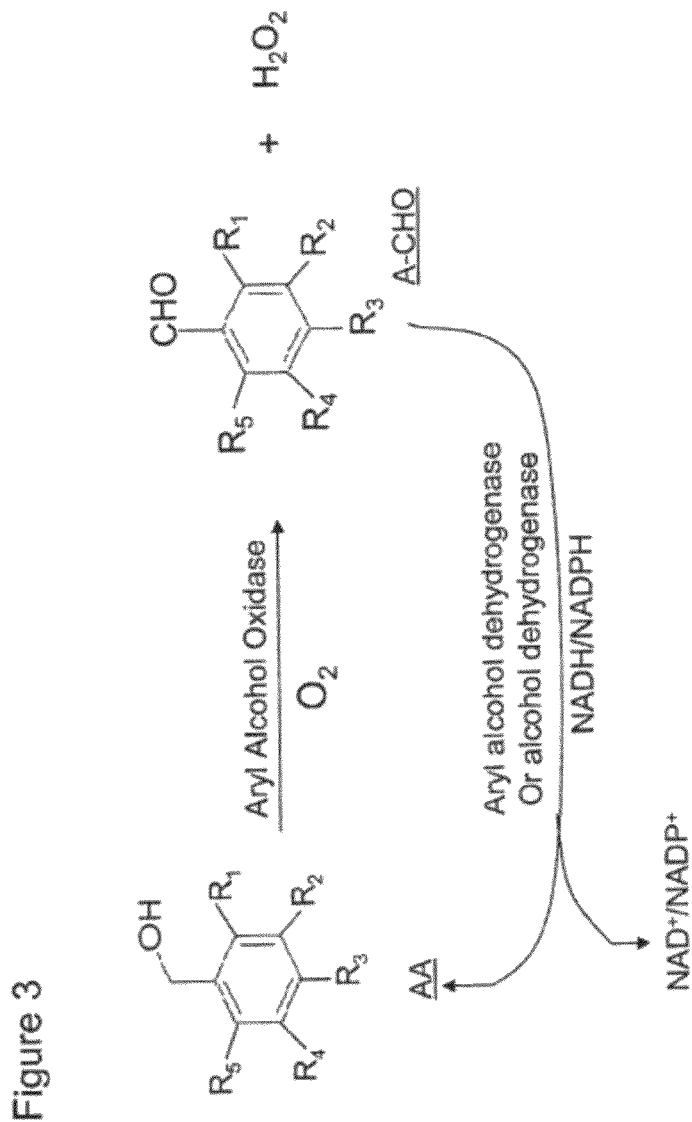
FIG. 3 illustrates use of aryl alcohol oxidase and oxygen to oxidize the benzylic alcohol produced by a hydrolytic enzyme acting on a hydrolytic enzyme substrate of the invention to form a benzaldehyde and hydrogen peroxide, followed by a reduction of the benzaldehyde back to the benzylic alcohol. The reduction uses NADH or NADPH and an alcohol dehydrogenase, producing NAD+ or NADP+.

The present invention provides for substrates for hydrolytic enzymes that provide for a highly efficient enzyme activity detection system. The substrates include a recognition moiety that make them specifically recognizable by the hydrolytic enzyme of interest, and that can function as part of the substrate for the hydrolytic enzyme. The recognition moiety is covalently linked to a molecular fragment that can be cleaved off by the action of the hydrolytic enzyme. Suitable examples of these substrates are depicted in FIGS. 1-9.

For clarity of disclosure, and not by way of limitation, the detailed description of the invention is divided into the subsections that follow.

A. DEFINITIONS

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, "blood sample" refers to a whole blood sample or a plasma or serum fraction derived therefrom. Preferably, the blood sample refers to a human blood sample such as whole blood or a plasma or serum fraction derived therefrom. Also preferably, the blood sample is pre-treated before the assay by removing substantially all hemoglobin (i.e., red blood cells) in order to eliminate or significantly reduce the oxidative interference from the hemoglobin molecules.

As used herein the term "whole blood" refers to a blood sample that has not been fractionated and contains both cellular and fluid components. As used herein, "whole blood" refers to freshly drawn blood which is tested before it clots, or a conventionally-drawn blood sample, which may be drawn into a vacutainer, and which may contain an anticoagulant, such as lithium-heparin, EDTA, etc., or to which one or more other standard clinical agents may be added in the course of routine clinical testing.

As used herein, the phrase "substantially all hemoglobin has been removed" refers to a blood sample wherein preferably at least about 50%, 60% or 70%, more preferably, at least about 80%, 90% or 95%, and most preferably, at least about 96%, 97%, 98%, 99 or 100% of all hemoglobin-containing red blood cells in the sample have been removed to eliminate or significantly reduce the oxidative interference from hemoglobin.

As used herein, the term "plasma" refers to the fluid, non-cellular component of the whole blood. Depending on the separation method used, plasma may be completely free of cellular components, or may contain various amounts of platelets and/or a small amount of other cellular components. Because plasma includes various clotting factors such as fibrinogen, the term "plasma" is distinguished from "serum" as set forth below.

As used herein, the term "serum" refers to whole mammalian serum, such as whole human serum. Further, as used herein, "serum" refers to blood plasma from which clotting factors (e.g., fibrinogen) have been removed.

As used herein, the term "fluid" refers to any composition that can flow. Fluids thus encompass compositions that are in the form of semi-solids, pastes, solutions, aqueous mixtures, gels, lotions, creams and other such compositions.

As used herein, the term "disease" or "disorder" refers to a pathological condition in an organism resulting from, e.g., infection or genetic defect, and characterized by identifiable symptoms.

As used herein, "contacting" means bringing two or more components together. "Contacting" can be achieved by mixing all the components in a fluid or semi-fluid mixture. "Contacting" can also be achieved when one or more components are brought into contact with one or more other components on a solid surface such as a solid tissue section or a substrate.

As used herein, the term "chromogenic substrate" refers to a chemical composition that can participate in a particular enzymatic reaction as either a donor or an acceptor for the reaction and that changes color during the reaction. For example, myeloperoxidase converts hydrogen peroxide to water by borrowing two hydrogen atoms from a donor molecule. When the donor molecule is a chromogenic substrate, the oxidation of the chromogenic substrate causes the substrate to change to a detectable color. For example, 3,3',5,5'-tetramethylbenzidine (TMB) is colorless in the reduced state but blue in the oxidized state or yellow in the diamine state.

As used herein, the term "non-chromogenic co-substrate" refers to a chemical composition that participates in the same enzymatic reaction as the chromogenic substrate but does not change color during the reaction. In the example above, hydrogen peroxide is a non-chromogenic co-substrate because both water and hydrogen peroxide are colorless.

As used herein, the term "comparing" generally means examining in order to note similarities or differences between two or more values. Preferably, "comparing" refers to quantitative comparisons such as, for example, subtracting one value from another, calculating a ratio of two values, calculating a percentage of one value with respect to another, or combining these types of calculations to produce a single number. As used herein, "comparing" further refers to comparisons made by a human, comparisons made by a computer or other processor, and comparisons made by a human in combination with a computer or other processor.

As used herein, the terms "alkyl," "alkenyl" and "alkynyl" unless otherwise indicated include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C or as C1-C10 or C1-10. When heteroatoms (e.g., N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described.

Typically, the alkyl, alkenyl and alkynyl substituents of the invention contain 1-10C (alkyl) or 2-10C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

The terms "1-alkene" and "1-alkyne" as used herein refer to an alkene or alkyne respectively that is attached to a base molecule being described through a carbon atom that is double or triple bonded to an adjacent carbon atom of the alkene or alkyne moiety.

Alkyl, alkenyl and alkynyl groups are often substituted to the extent that such substitution makes sense chemically. Typical substituents include, but are not limited to, halo, $=O$, $=N-CN$, $=N-OR$, $=NR$, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C3-C8 heterocyclyl, C4-C10 heterocyclyclalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, $=O$, $=N-CN$, $=N-OR'$, $=NR'$, OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$, wherein each R' is independently H, or an unsubstituted group selected from C1-C8 alkyl, C2-C8 heteroalkyl, C3-C8 heterocyclyl, C4-C10 heterocyclyclalkyl, C1-C8 acyl, C2-C8 heteroacyl, C6-C10 aryl and C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two R or R' groups on the same or adjacent atoms (e.g., $-NR_2$, or $-NR-C(O)R$), the two R or R' groups can optionally be taken together with the atoms in the substituent group to which they are attached to form a ring having 5-8 ring members, which can be substituted as allowed for the R or R' itself, and can contain an additional heteroatom (N, O or S) as a ring member.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to specifically describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" (or the equivalent term 'heterocycloalkyl') may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to C5-C6 monocyclic or C8-C10 fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5 or 6 ring members, and the bicyclic heteroaryls contain 8, 9 or 10 ring members.

Aryl and heteroaryl moieties may be substituted with a variety of substituents including C1-C8 alkyl, C2-C8 alkenyl, C2-C8 alkynyl, C3-C8 cycloalkyl, C5-C12 aryl, C1-C8 acyl, and heteroforms of these, each of which can itself be further substituted; other substituents for aryl and heteroaryl moieties include halo, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclyclalkyl, C6-C10 aryl, C5-C10 heteroaryl, C7-C12 arylalkyl, or C6-C12 heteroarylalkyl, and each R is optionally substituted as described above for alkyl groups. Where a substituent group contains two R or R' groups on the same or adjacent atoms (e.g., —NR2, or —NR—C(O)R), the two R or R' groups can optionally be taken together with the atoms in the substituent group to which they are attached to form a ring having 5-8 ring members, which can be substituted as allowed for the R or R' itself, and can contain an additional heteroatom (N, O or S) as a ring member. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —(CH$_2$)$_n$— where n is 1-8 and preferably n is 1-4, though where specified, an alkylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, alkylene, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, $R^7$ is optionally substituted alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

"Halo", as used herein includes fluoro, chloro, bromo and iodo. Fluoro and chloro are often preferred.

"Amino" as used herein refers to NH$_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

"Amino acid" as used herein refers to an amino substituted carboxylic acid compound; typical examples are the 20 common alpha-amino acids, as well as analogs thereof having the amine in the beta or gamma position relative to the carboxylic acid. "Alpha-amino acid" as used herein refers to an amino acid of the formula HO$_2$C—CH(NH$_2$)—R$^a$, where R$^a$ is an optionally substituted C1-C6 alkyl group, or optionally substituted aryl or arylalkyl group, or optionally substituted heteroaryl or heteroarylalkyl group. Specific examples include glycine, alanine, valine, leucine, isoleucine, serine, threonine, aspartic acid, glutamic acid, glutamine, phenylalanine, tyrosine, tryptophan, lysine, histidine, methionine, cysteine, arginine, asparagine, and proline.

"Saccharide" as used herein refers to a carbohydrate moiety containing one or more sugars, typically in a branched or unbranched chain of sugars. Saccharides are typically of the formula (CH$_2$O)$_n$, where n is an integer, such as 1-1000 or 3-50, or 5-25. Typical examples are glucose, sucrose, starches, and cellulose. These saccharides can be monosaccharides, disaccharides, or polysaccharides; the term 'oligosaccharides' is used to describe saccharides that consist of about 3 to 25 sugar groups, usually in an unbranched chain.

"A recognition component of a substrate for a hydrolytic enzyme" or a "recognition moiety" refers to a portion of an enzyme substrate molecule that is sufficiently similar to a portion of a natural substrate for the hydrolytic enzyme to cause the hydrolytic enzyme to bind to the enzyme substrate molecule.

As used herein, an "esterase" refers to an enzyme that splits esters into an acid and an alcohol in a chemical reaction with water called hydrolysis. A wide range of different esterases exist that differ in their substrate specificity, their protein structure, and their biological function. Exemplary esterases include acetylesterases, thiolester hydrolases, phosphoric monoester hydrolases (or phosphomonoesterases), phosphodiesterases, triphosphoric monoester hydrolases, sulfuric ester hydrolases (sulfatases), diphosphoric monoester hydrolases, phosphoric triester hydrolases, exonucleases (deoxyribonucleases and ribonucleases), and endonucleases (deoxyribonucleases and ribonucleases). It is intended to encompass esterase with conservative amino acid substitutions or functional fragments that do not substantially alter its activity.

As used herein, a "glycoside hydrolase (also called glycosidase)" refers to an enzyme that catalyzes the hydrolysis of the glycosidic linkage to release smaller sugars. Glycoside hydrolases are typically classified into EC 3.2.1 as enzymes catalyzing the hydrolysis of O- or S-glycosides. Glycoside hydrolases can also be classified according to the stereochemical outcome of the hydrolysis reaction: thus they can be classified as either retaining or inverting enzymes. Glycoside hydrolases can also be classified as exo or endo acting, dependent upon whether they act at the (usually non-reducing) end or in the middle, respectively, of an oligo/polysaccharide chain. Glycoside hydrolases may also be classified by sequence or structure based methods. Exemplary glycoside hydrolases include β-galactosidase (also called beta-gal or β-gal), glucosidase, xylannase, lactase, amylase, chitinase, sucrase, maltase, neuraminidase, invertase, hyaluronidase and lysozyme. It is intended to encompass glycoside hydrolase with conservative amino acid substitutions or functional fragments that do not substantially alter its activity.

As used herein, a "phosphatase" refers to an enzyme that removes a phosphate group from its substrate by hydrolysing phosphoric acid monoesters into a phosphate ion and a molecule with a free hydroxyl group. Phosphatases can be subdivided based upon their substrate specificity, such as tyrosine specific phosphatases, serine/threonine specific phosphatases, dual specificity phosphatases, histidine specific phosphatases and lipid phosphatases. Exemplary phosphatases include alkaline phosphatases (ALP, ALKP). It is intended to encompass phosphatase with conservative amino acid substitutions or functional fragments that do not substantially alter its activity.

As used herein, an "alcohol oxidase" refers to an enzyme that catalyzes the following chemical reaction:

a primary alcohol+$O_2$⇌an aldehyde+$H_2O_2$

The systematic name of this enzyme class is alcohol:oxygen oxidoreductase. This enzyme is also called ethanol oxidase. It is intended to encompass alcohol oxidase with conservative amino acid substitutions or functional fragments that do not substantially alter its activity.

As used herein, an "aryl alcohol oxidase" refers to an enzyme that catalyzes the following chemical reaction:

an aromatic primary alcohol+$O_2$⇌an aromatic aldehyde+$H_2O_2$

The systematic name of this enzyme class is aryl-alcohol: oxygen oxidoreductase. Other names in common use include veratryl alcohol oxidase, and arom. alcohol oxidase. It is intended to encompass aryl alcohol oxidase with conservative amino acid substitutions or functional fragments that do not substantially alter its activity.

As used herein, an "aryl alcohol dehydrogenase" refers to an enzyme that catalyzes the following chemical reaction:

an aromatic alcohol+$NAD^+$⇌an aromatic aldehyde+$NADH+H^+$

The systematic name of this enzyme class is aryl-alcohol: NAD+ oxidoreductase. Other names in common use or examples include p-hydroxybenzyl alcohol dehydrogenase, benzyl alcohol dehydrogenase, and coniferyl alcohol dehydrogenase. It is intended to encompass aryl alcohol dehydrogenase with conservative amino acid substitutions or functional fragments that do not substantially alter its activity.

As used herein, an "alcohol dehydrogenase (ADH)" refers to a group of dehydrogenase enzymes that occur in many organisms and facilitate the interconversion between alcohols and aldehydes or ketones with the reduction of $NAD^+$ to NADH. It is intended to encompass alcohol dehydrogenase with conservative amino acid substitutions or functional fragments that do not substantially alter its activity.

As used herein the term "assessing" is intended to include quantitative and qualitative determination in the sense of obtaining an absolute value for the amount or concentration of the analyte present in the sample, and also of obtaining an index, ratio, percentage, visual or other value indicative of the level of analyte in the sample. Assessment may be direct or indirect and the chemical species actually detected need not of course be the analyte itself but may for example be a derivative thereof or some further substance.

As used herein, a "binding reagent (or binder)" refers to any substance that binds to target or analyte with desired affinity and/or specificity. Non-limiting examples of the binding reagent include cells, cellular organelles, viruses, particles, microparticles, molecules, or an aggregate or complex thereof, or an aggregate or complex of molecules.

As used herein, "antibody" includes not only intact polyclonal or monoclonal antibodies, but also fragments thereof (such as Fab, Fab', F(ab')$_2$, Fv), single chain (ScFv), a diabody, a multi-specific antibody formed from antibody fragments, mutants thereof, fusion proteins comprising an antibody portion, and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class.

As used herein, the term "specifically binds" refers to the specificity of a binding reagent, e.g., an antibody, such that it preferentially binds to a defined analyte or target. Recognition by a binding reagent or an antibody of a particular analyte or target in the presence of other potential targets is one characteristic of such binding. In some embodiments, a binding reagent that specifically binds to an analyte avoids binding to other interfering moiety or moieties in the sample to be tested.

As used herein the term "avoids binding" refers to the specificity of particular binding reagents, e.g., antibodies or antibody fragments. Binding reagents, antibodies or antibody fragments that avoid binding to a particular moiety generally contain a specificity such that a large percentage of the particular moiety would not be bound by such binding reagents, antibodies or antibody fragments. This percentage generally lies within the acceptable cross reactivity percentage with interfering moieties of assays utilizing the binding reagents or antibodies directed to detecting a specific target. Frequently, the binding reagents, antibodies or antibody fragments of the present disclosure avoid binding greater than about 90% of an interfering moiety, although higher percentages are clearly contemplated and preferred. For example, binding reagents, antibodies or antibody fragments of the present disclosure avoid binding about 91%, about 92%, about 93%, about 94%, about 95%, about 96%, about 97%, about 98%, about 99%, and about 99% or more of an interfering moiety. Less occasionally, binding reagents, antibodies or antibody fragments of the present disclosure avoid binding greater than about 70%, or greater than about 75%, or greater than about 80%, or greater than about 85% of an interfering moiety.

As used herein, "mammal" refers to any of the mammalian class of species. Frequently, the term "mammal," as used herein, refers to humans, human subjects or human patients.

As used herein, the term "subject" is not limited to a specific species or sample type. For example, the term "subject" may refer to a patient, and frequently a human patient. However, this term is not limited to humans and thus encompasses a variety of mammalian species.

As used herein, "stringency" of nucleic acid hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see *Current Protocols in Molecular Biology* (Ausubel et al. eds., Wiley Interscience Publishers, 1995); *Molecular Cloning: A Laboratory Manual* (J. Sambrook, E. Fritsch, T. Maniatis eds., Cold Spring Harbor Laboratory Press, 2d ed. 1989); Wood et al., *Proc. Natl. Acad. Sci. USA,* 82:1585-1588 (1985).

As used herein the term "isolated" refers to material removed from its original environment, and is altered from its natural state. For example, an isolated polypeptide could be coupled to a carrier, and still be "isolated" because that polypeptide is not in its original environment.

As used herein, "test substance (or candidate compound)" refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on a target is determined by the disclosed and/or claimed methods herein.

As used herein, high-throughput screening (HTS) refers to processes that test a large number of samples, such as samples of diverse chemical structures against disease targets to identify "hits" (see, e.g., Broach, et al., High throughput screening for drug discovery, *Nature,* 384:14-16 (1996); Janzen, et al., High throughput screening as a discovery tool in the pharmaceutical industry, *Lab Robotics Automation:* 8261-265 (1996); Fernandes, P. B., Letter from the society president, *J. Biomol. Screening,* 2:1 (1997); Burbaum, et al., New technologies for high-throughput screening, *Curr. Opin. Chem. Biol.,* 1:72-78 (1997)). HTS operations are highly automated and computerized to handle sample preparation, assay procedures and the subsequent processing of large volumes of data.

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "bacteria" refers to small prokaryotic organisms (linear dimensions of around 1 micron) with non-compartmentalized circular DNA and ribosomes of about 70S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are three main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to an obligate intracellular parasite of living but non-cellular nature, consisting of DNA or RNA and a protein coat. Viruses range in diameter from about 20 to about 300 nm Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "fungus" refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

As used herein, $NAD^+$ refers to nicotinamide adenine dinucleotide or a suitable derivative such as acetyl-$NAD^+$ or thio-$NAD^+$. NADH refers to the reduced form of $NAD^+$ and a suitable derivative such as acetyl-NADH or thio-NADH. NADP refers to nicotinamide adenine dinucleotide phosphate or a suitable derivative such as acetyl-$NADP^+$ or thio-$NADP^+$. NADPH refers to the reduced form of NADP and a suitable derivative such as acetyl-NADPH or thio-NADPH.

B. HYDROLYTIC ENZYMES

Enzymes are catalytic proteins that act on substrate(s) to yield product(s). hydrolytic enzymes or hydrolases are enzymes that catalyze the hydrolysis of a chemical bond by addition of water. For example, an enzyme that catalyzes the following reaction is a hydrolase: $A-B+H_2O \rightarrow A-OH+B-H$. In enzymology, hydrolases are typically classified as EC 3 in the EC number classification of enzymes. It is intended to encompass hydrolase with conservative amino acid substitutions or functional fragments that do not substantially alter its activity.

Hydrolases can be further classified into several subclasses based upon the bonds that they act upon: for example, EC3.1: ester bonds (esterases, nuclease, phosphodiesterase, lipase, phosphatase); EC3.2: sugars (glycoside hydrolases); EC 3.3: ether bonds; EC 3.5: carbon-nitrogen bonds, other than peptide bonds; EC. 3.6: acid anhydrides (acid anhydride hydrolases, including helicases and GTPase); EC 3.7: carbon-carbon bonds; EC 3.8: halide bonds; EC 3.9: phosphorous-nitrogen bond; EC 3.10: sulfur-nitrogen bonds; EC 3.11: carbon-phosphorous bonds; EC 3.12: sulfur-sulfur bonds; EC 3.13: carbon-sulfur bonds The methods described herein can be used with any suitable hydrolytic enzyme, i.e., any enzyme that splits a substrate molecule into two products, one of which is a hydroxylated organic molecule, while adding a molecule of water. Glycosidases, esterases, lipases, nucleases, and phosphatases are typical examples. The glycosidases hydrolyze a glycosylated alcohol to produce a sugar and the free alcohol. Esterases hydrolyze an ester to produce a carboxylic acid and a free alcohol. Phosphatases typically hydrolyze a phosphate ester to produce phosphate (or diphosphate or triphospate) and an alcohol.

Some glycosidases of special interest include beta-D-galactosidase Some esterases of special interest include alpha-amino acid esterases, carboxylesterases, acetylesterases, and the like. Some phosphatases of special interest include alkaline phosphatase, which can be easily conjugated to a carrier or antibody, phosphodiesterases, and the like. Bovine alkaline phosphatase is one suitable example, which is well known for use in ELISA assays.

C. HYDROLYTIC ENZYME SUBSTRATES

The hydrolytic enzyme substrates of the invention generally comprise an alcohol that is linked by a cleavable linkage to a recognition moiety that is recognized by the hydrolytic enzyme as part of its substrate. The recognition moiety renders the hydrolytic enzyme substrate specific for the chosen hydrolytic enzyme, e.g., the recognition moiety makes the substrate susceptible to transformation by the chosen hydrolytic enzyme and not subject to transformation at comparable rates by other enzymes that may be present in a typical system.

Figure 4:
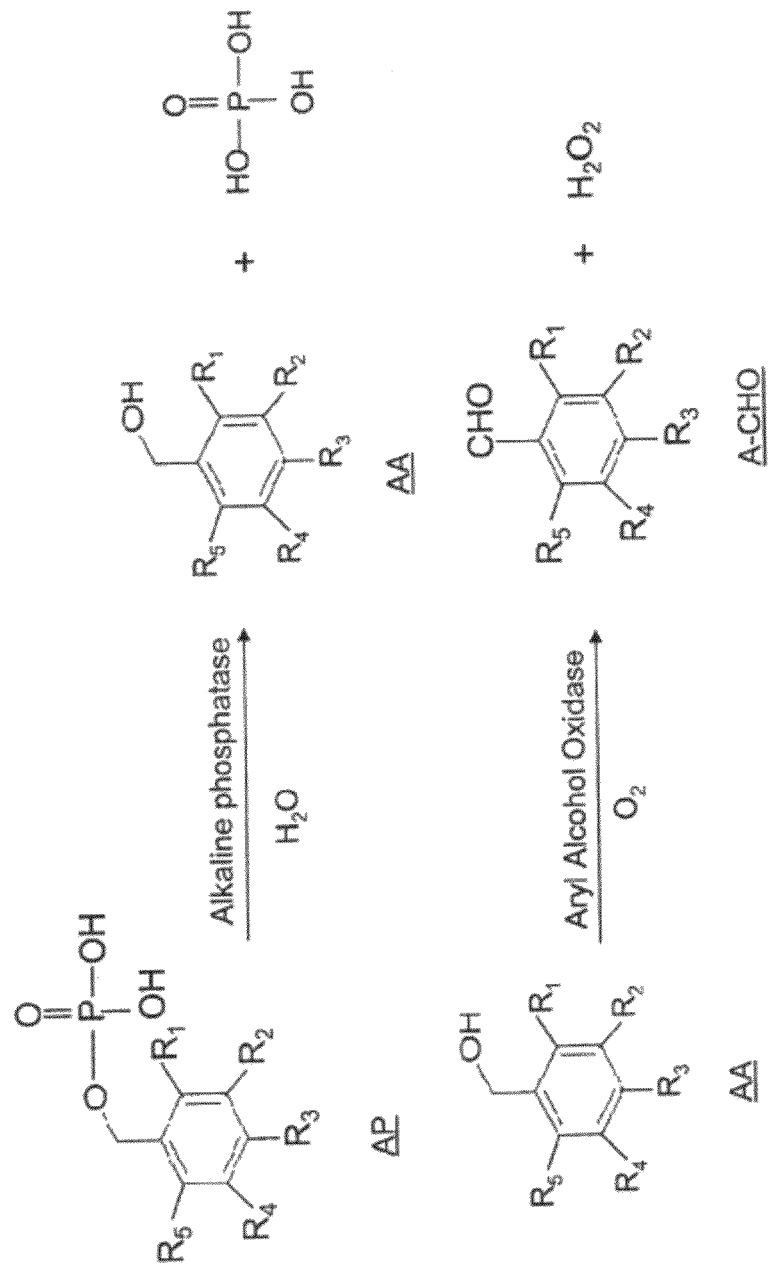
FIG. 4 illustrates a benzylic phosphate ester as a hydrolytic enzyme substrate, hydrolyzed by alkaline phosphatase to produce phosphate and a benzylic alcohol. The benzylic alcohol is then oxidized by aryl alcohol oxidase and oxygen to produce benzaldehyde and hydrogen peroxide; hydrogen peroxide formation can be monitored to measure the rate of the reaction and thus detect and/or quantify the amount of alkaline phosphatase present.
Figure 5:
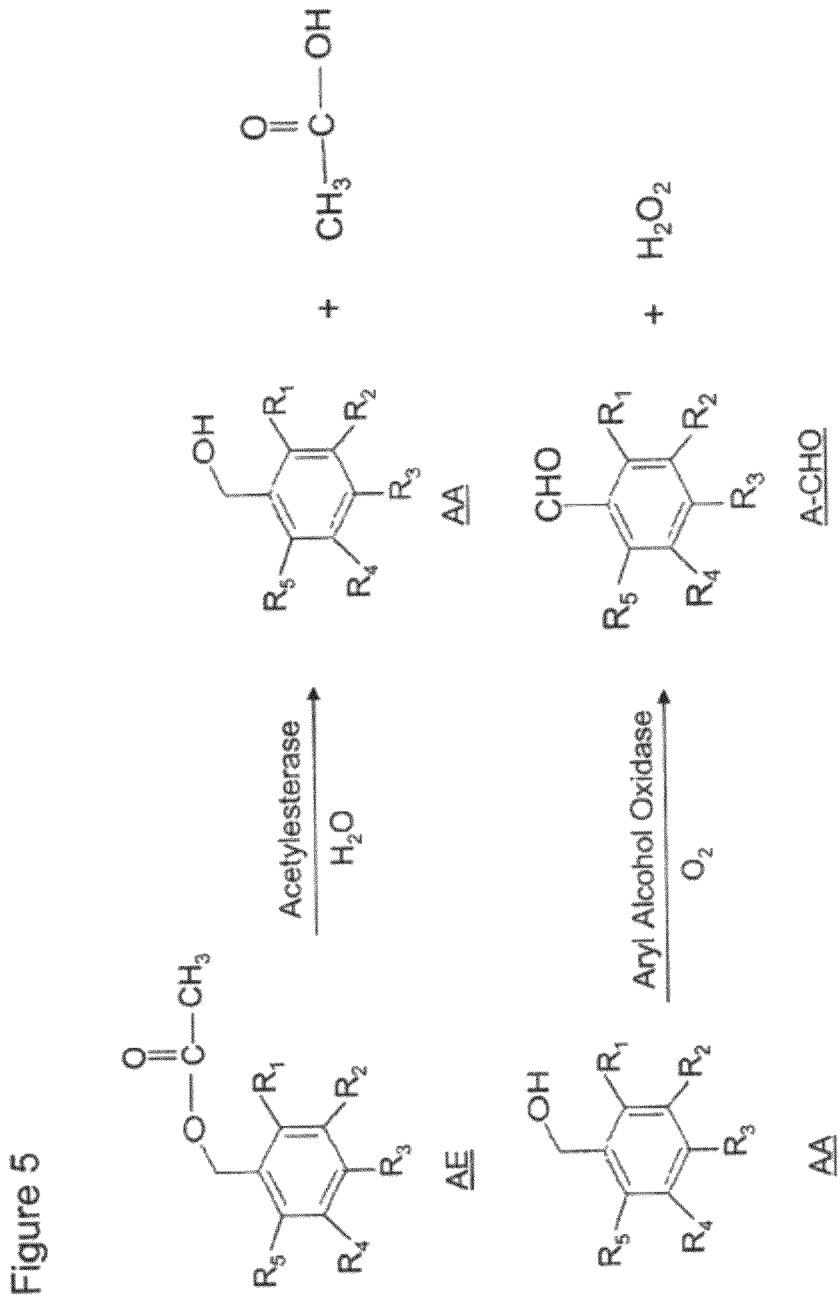
FIG. 5 illustrates a benzylic ester acting as a hydrolytic enzyme substrate for an acetylesterase, releasing a benzylic alcohol, which is then oxidized by an additional enzyme such as aryl alcohol oxidase and oxygen. The reaction products include a benzaldehyde and hydrogen peroxide, which can be measured by methods known in the art.
Figure 6:
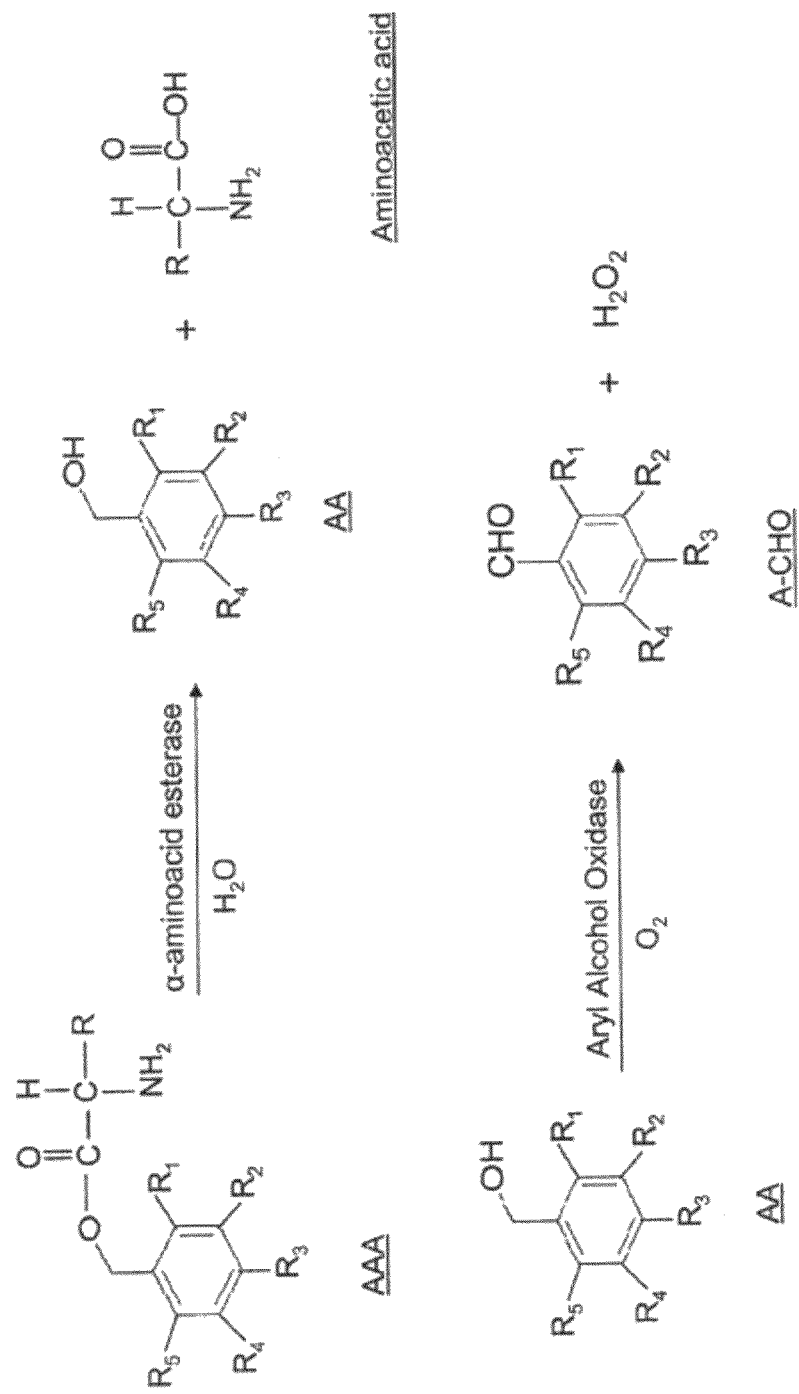
FIG. 6 illustrates a benzylic ester of an alpha-amino acid acting as a hydrolytic enzyme substrate for an alpha-amino acid esterase. The enzymatic reaction releases a benzylic alcohol, which is then oxidized by an additional enzyme such as aryl alcohol oxidase and oxygen. The reaction products include a benzaldehyde and hydrogen peroxide, which can be measured by methods known in the art.
Figure 7:
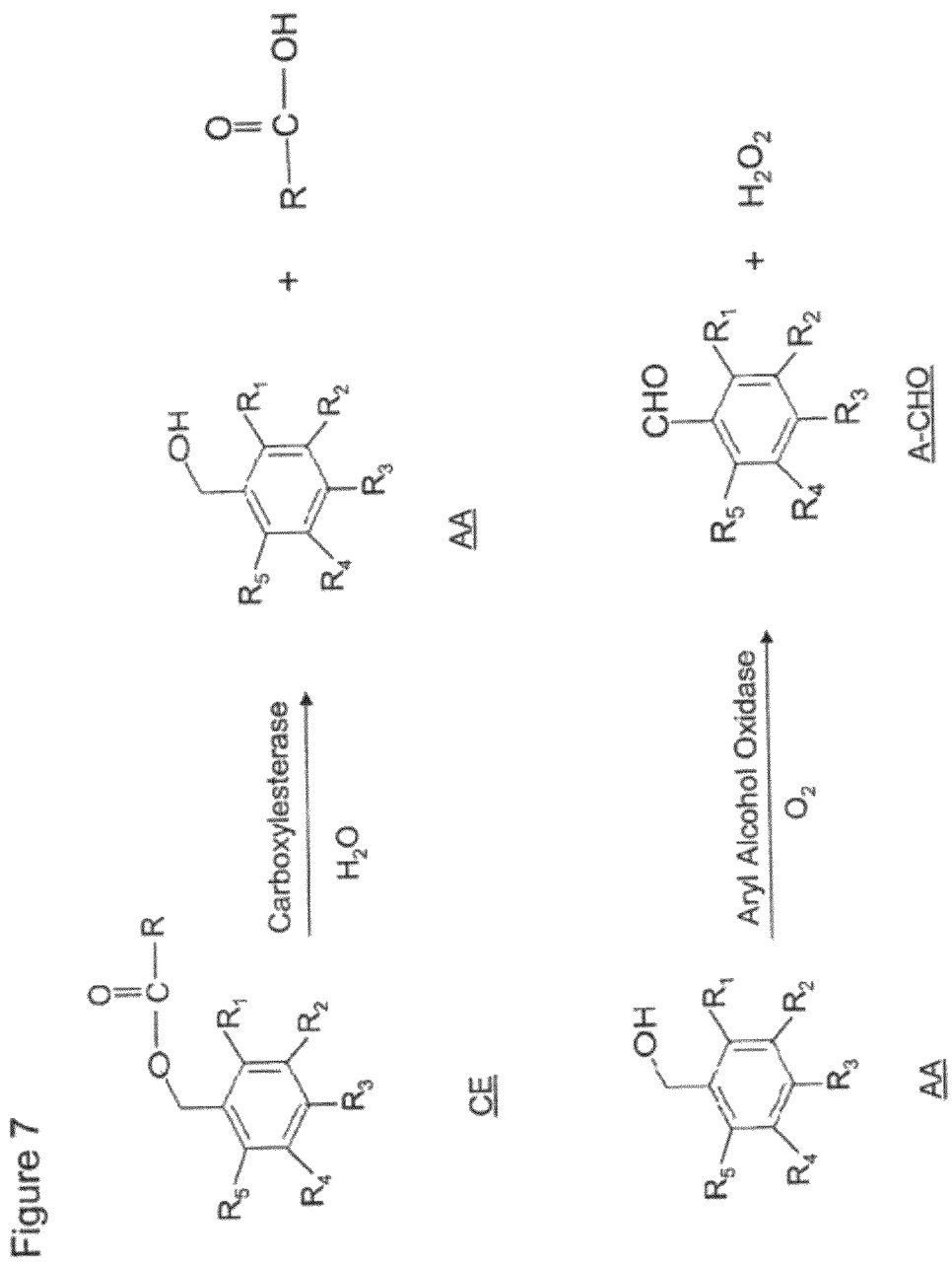
FIG. 7 illustrates a benzylic ester acting as a hydrolytic enzyme substrate for a carboxylesterase, releasing a benzylic alcohol, which is then oxidized by an additional enzyme such as aryl alcohol oxidase and oxygen. The reaction products include a benzaldehyde and hydrogen peroxide, which can be measured by methods known in the art.
Figure 8:
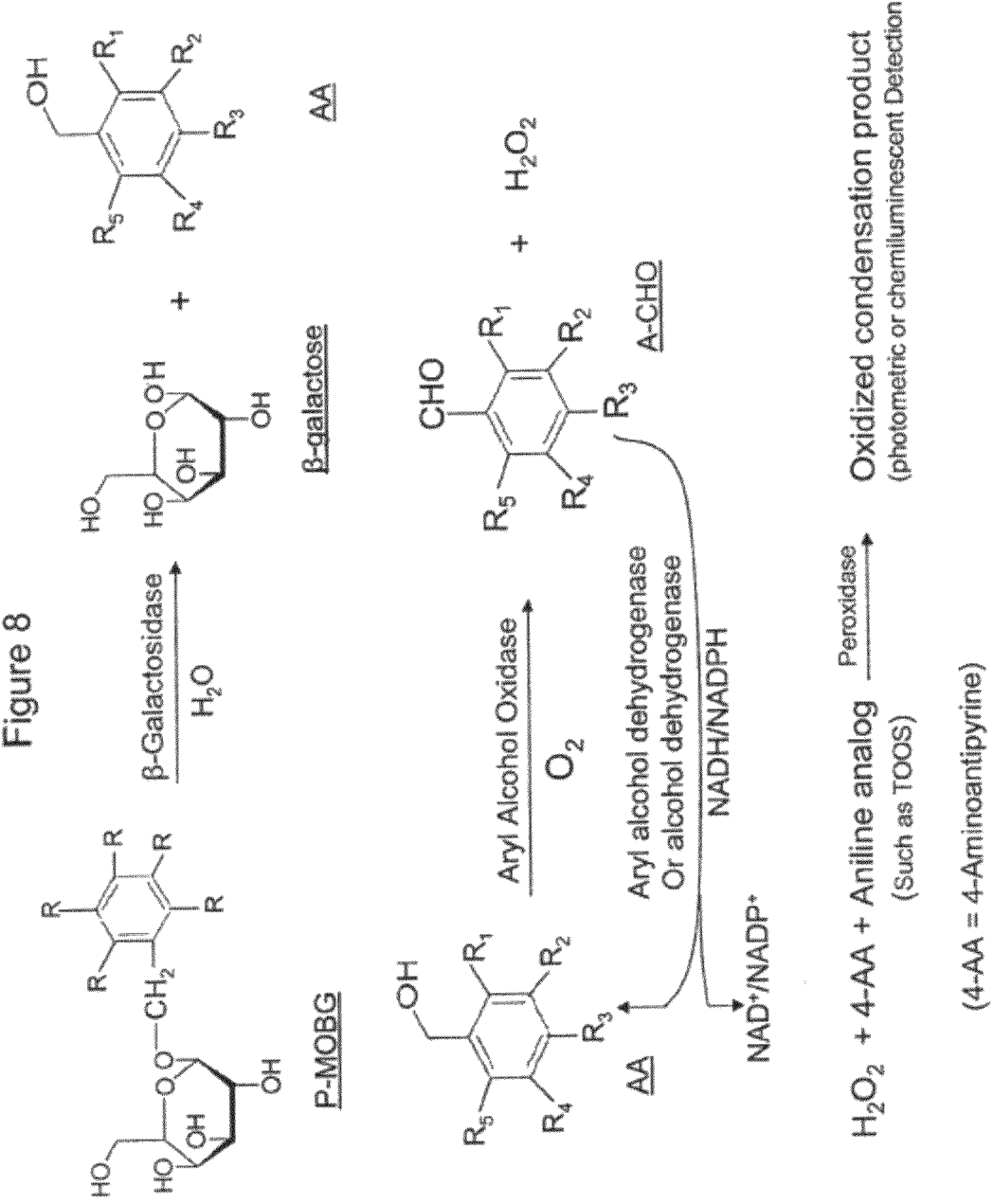
FIG. 8 illustrates a beta-galactosidase substrate as shown in FIG. 1, and illustrates the option of using a reductive enzyme (aryl alcohol dehydrogenase or alcohol dehydrogenase) to reduce the benzaldehyde produced in FIG. 1, providing a cycling enzyme system. The reduction step regenerates the benzylic alcohol and produces an oxidized co-factor (NAD+ or NADP+), so the rate of consumption of reduced co-factor or the rate of formation of the oxidized co-factor can be monitored to measure the amount of beta-galactosidase present. Alternatively or in addition, as shown in FIG. 8, a Trinder reaction can be used to measure the hydrogen peroxide produced to determine the amount of beta-galactosidase present.
Figure 9:
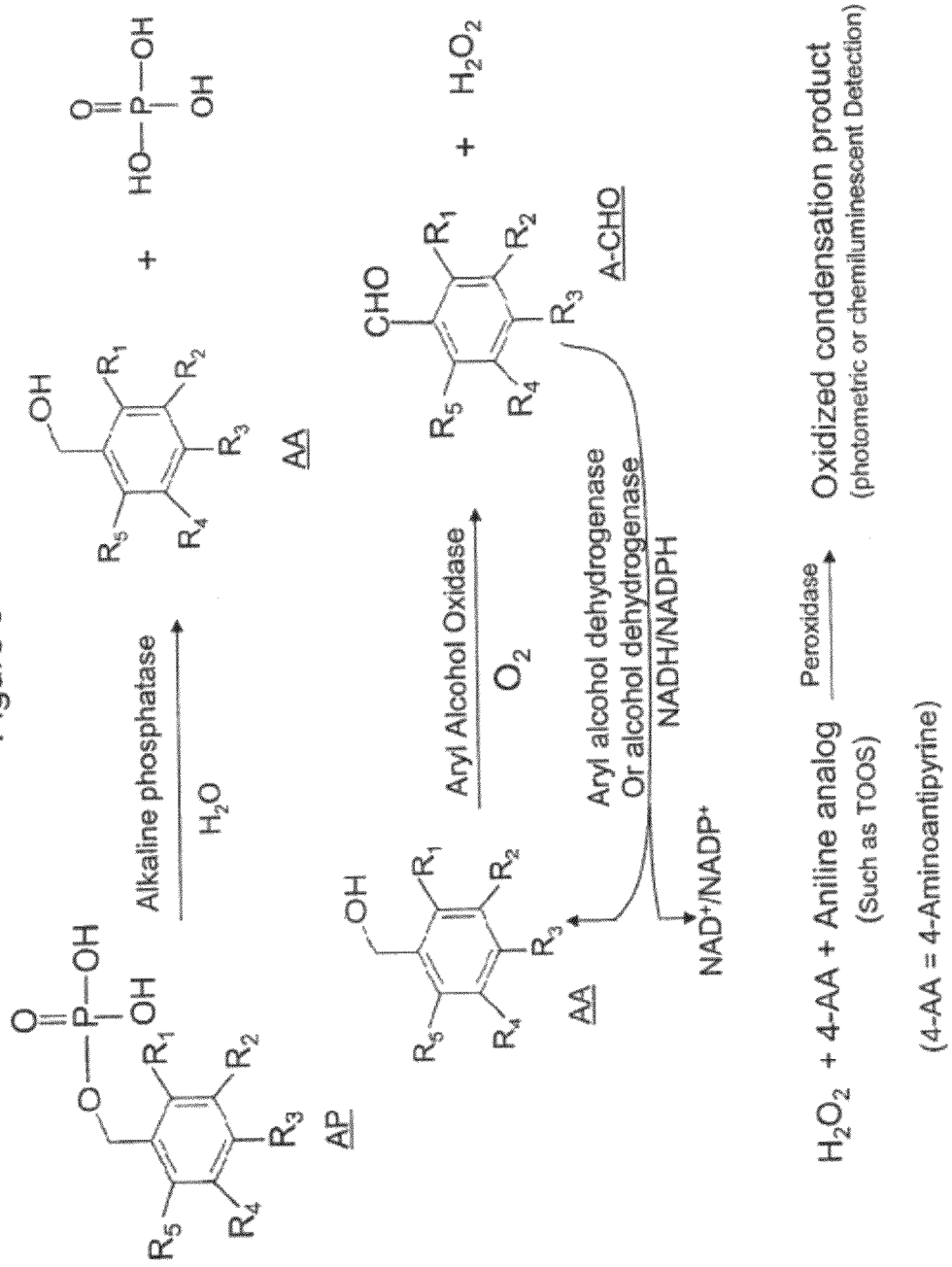
FIG. 9 illustrates a benzylic phosphate ester as a hydrolytic enzyme substrate, reacting with alkaline phosphatase to produce phosphate and a benzylic alcohol. The benzylic alcohol is then oxidized by aryl alcohol oxidase and oxygen to produce benzaldehyde and hydrogen peroxide, as shown in FIG. 4.

Examples of recognition moieties for some specific hydrolytic enzymes are shown in FIGS. 1-9. The galactosyl ring of the substrate shown in FIG. 1.1 is a recognition moiety that makes the benzylic substrate specifically recognizable by and hyrolyzable by beta-D-galactosidase. Similarly, the phosphate of the substrate in FIG. 4 makes that hydrolytic enzyme substrate specifically susceptible to hydrolytic action of alkaline phosphatase; the acetyl ester of the substrate in FIG. 5 provides a substrate selectively recognized by acetylesterase; and the alpha-amino acid ester of the substrate in FIG. 6 provides a substrate that is selectively hydrolyzed by alpha-amino acid esterase activity.

Typically, the hydrolytic enzyme substrates are not a substrate for the additional enzyme or enzymes used in the assay methods described herein (aryl alcohol oxidase, alcohol dehydrogenase, aryl alcohol dehydrogenase, etc.); only after the substrate is hydrolyzed by a suitable hydrolytic enzyme does it serve as a substrate for the oxidizing and/or reducing enzymes that are used in the assay systems described herein.

The hydrolytic enzyme substrates of the invention include compounds of Formula (I):

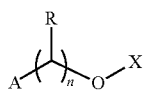

(I)

wherein:
A is an aromatic or heteroaromatic group, a 1-alkene or a 1-alkyne, each of which is optionally substituted;
each R is independently H or an optionally substituted C1-C4 alkyl or aryl;
n is an integer from 1-4;
and X is a group comprising a substrate moiety,
wherein the substrate moiety comprises a recognition component of a substrate for the hydrolytic enzyme, and wherein the activity of the hydrolytic enzyme is capable of hydrolyzing the compound of formula (I) to form a detectable product of Formula II:

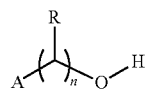

(II)

In some embodiments, the reaction of the hydrolytic enzyme with the hydrolytic enzyme substrate of Formula (I) produces a compound of formula (II) and a by-product of Formula (III):

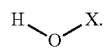

(III)

'X' in these compounds includes a recognition moiety for the particular hydrolytic enzyme of interest. Examples of the by-products of Formula (III) can be seen in FIGS. 1-9. These include galactose, phosphate, carboxylic acids, amino acids, and the like.

In some embodiments of the hydrolytic enzyme substrates of the invention, A is an optionally substituted aromatic or heteroaromatic group. Suitable aromatic groups include phenyl and naphthyl. Suitable heteroaromatic groups include pyridyl, pyrimidinyl, triazinyl, indolyl, imidazolyl, benzimidazolyl, pyrazolyl, benzopyrazolyl, quinolinyl, isoquinolinyl, thienyl, furanyl, pyrrolyl, oxazolyl, isoxazolyl, thiazolyl, and isothiazolyl, as examples. These aryl and heteroaryl groups can be substituted as further described herein, or they can be unsubstituted.

In other embodiments of the hydrolytic enzyme substrates of the invention, A is a 1-alkene or a 1-alkyne. In some embodiments, it is a 1-alkene of the formula (IV):

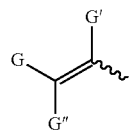

(IV)

wherein the wavy line indicates the point of attachment of A to —[CH(R)]$_n$—O—X in Formula (I), and each G, G' and G" is independently H or an optionally substituted group selected from the group consisting of C1-C8 alkyl, C2-C8 alkenyl, C2-C8 alkynyl, C3-C8 cycloalkyl, C3-C8 heterocycloalkyl, aryl, and heteroaryl. In certain of these embodiments, A is a group of Formula (IVb):

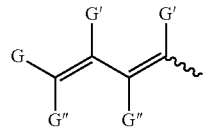

(IVb)

where G, G' and G" are defined as for Formula (IV). An example of this type of compound is shown as HDEGP in the examples.

In other embodiments of the hydrolytic enzyme substrate, A is a 1-alkyne of the formula (V):

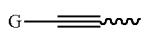

wherein the wavy line indicates the point of attachment of A to —[CH(R)]$_n$—O—X in Formula (I), and G is H or an optionally substituted member selected from the group consisting of C1-C8 alkyl, C2-C8 alkenyl, C2-C8 alkynyl, C3-C8 cycloalkyl, C3-C8 heterocycloalkyl, aryl, and heteroaryl. In some such embodiments, G can be optionally substituted phenyl.

In any of the foregoing embodiments, R can be H, Methyl or phenyl, for example. In preferred embodiments, R is H, so the product of Formula (II) is a primary alcohol. Where n is 1, this product becomes a benzylic alcohol when A is phenyl, an allylic alcohol when A is a 1-alkene, or a propargylic alcohol when A is a 1-alkyne. Preferred embodiments include compounds wherein R is H and n is 1.

In some embodiments of the hydrolytic enzyme substrates of the invention, X comprises a saccharide, e.g., a monosaccharide or a disaccharide. In some embodiments, X is a D-galactosyl ring or another D-sugar such as glucose, allose, mannose, xylose, gulose, talose, altrose, idose, ribose, arabinose, lyxose, and the like. In some embodiments, the hydrolytic enzyme substrate is a compound of Formula (VIa) or (VIb):

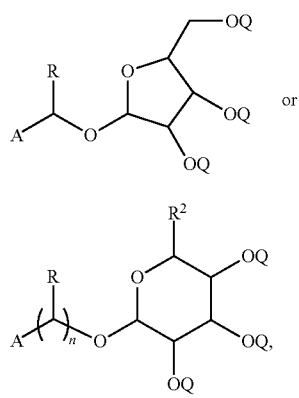

wherein R$^2$ is H or —CH$_2$OQ, and each Q is independently H or a monosaccharide, disaccharide or oligosaccharide, and A, R and n are as defined for Formula (I). In some embodiments, each Q is H; in some embodiments, n is 1; R can be H, and in some embodiments, R$^2$ is —CH$_2$OH or H.

In other embodiments, the hydrolytic enzyme substrate is an ester of formula (VII):

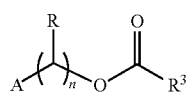

wherein R$^3$ is H or an optionally substituted aryl, heteroaryl, C1-C8 alkyl, C3-C8 cycloalkyl, or C3-C8 heterocyclyl group, and A, R and n are as defined for Formula (I).

R$^3$ in these compounds can vary widely, provided it acts as a recognition moiety for the hydrolytic enzyme of interest. In specific embodiments, R$^3$ is selected from the group consisting of Me, Et, and phenyl, or it is an amino acid radical such that HO$_2$C—R$^3$ is an alpha-amino acid. Thus —R$^3$ can be a group of the formula —CH(NH$_2$)—R$^{aa}$, where R$^{aa}$ is the side chain of one of the 20 commonly recognized essential amino acids. In some of these embodiments, n is 1.

In other embodiments, the hydrolytic enzyme substrate can be a compound of formula (VIII):

wherein Z is N, S, S=O, P, or P—OH, and R$^4$ is O, hydroxy, C1-C4 alkoxy, C1-C4 alkyl, or aryl. These can be, for example, phosphatase substrates, e.g., compounds of Formula I, wherein X comprises a phosphate group, so that Z in Formula (VII) is P—OH. Examples of these would be a compound of the formula (IX):

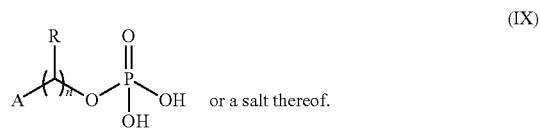

In the foregoing hydrolytic enzyme substrates, n can be 1; and wherever A can be an aryl group, it can be an optionally substituted phenyl group. In these embodiments, the phenyl group can be unsubstituted, or it can be substituted with 1-3 groups selected from halo, hydroxy, CN, NO$_2$, COOR', CONR'$_2$, NR'$_2$, OR', optionally substituted C1-4 alkyl, SR', SO$_2$R', or SO$_2$NR'$_2$, wherein each R' is independently H or optionally substituted C1-4 alkyl, and two R' on the same or adjacent atoms can be taken together to form an optionally substituted C3-C8 heterocyclic ring.

In additional embodiments of the hydrolytic enzyme substrates, A can be a group of the formula (X):

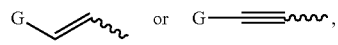

wherein the wavy line indicates the point of attachment of A to —[CH(R)]$_n$—O—X in Formula (I), and each G is independently H or an optionally substituted group selected from the group consisting of C1-C8 alkyl, C2-C8 heteroalkyl, C2-C8 alkenyl, C2-C8 alkynyl, C3-C8 cycloalkyl, C3-C8 heterocycloalkyl, aryl, and heteroaryl.

In any of the foregoing embodiments, the optional substituents for alkyl, alkenyl alkynyl, and heterocyclic groups can be as set forth below; or they can be selected from halo, oxo, CN, NO$_2$, COOR", CONR"$_2$, NR"$_2$, OR", optionally substituted C1-4 alkyl, SR', SO$_2$R", or SO$_2$NR"$_2$, wherein each R" is independently H or C1-4 alkyl. Likewise the optional substituents for aryl and heteroaryl groups can be as described in the definitions herein, or they can be selected from halo, CN, NO$_2$, COOR", CONR"$_2$, NR"$_2$, OR", optionally substituted C1-4 alkyl, SR', SO$_2$R", or SO$_2$NR"$_2$, wherein each R" is independently H or C1-4 alkyl.

In preferred embodiments of any of the foregoing hydrolytic enzyme substrates, R is H; and n is 1.

Preferred hydrolytic enzymes for the substrates of the invention include glycosidases; esterases; beta-D-galactosidase; alpha-amino acid esterases; and phosphatases. Suitable esterases can be a carboxylesterase, an acetyl esterase or an alpha-amino acid esterase.

D. HYDROLYTIC ENZYME SUBSTRATE COMPOSITIONS

The hydrolytic enzyme substrates of the invention can be used in combination with at least one additional enzyme, besides the hydrolytic enzyme that hydrolyzes the substrate. The additional enzyme is one that promotes efficient detection of the initial product of the hydrolytic enzyme activity, the compound of Formula (II), by converting it into another species. Therefore compositions that include the hydrolytic enzyme substrates described above and at least one additional enzyme are useful as components of an assay system for detecting and/or quantifying the presence of the hydrolytic enzymes of interest. Similarly, combinations of the hydrolytic enzyme substrate with other materials that are required in some embodiments of the methods described herein are also useful for these assays and are also an aspect of the invention.

Thus in another aspect, the invention provides compositions that comprise any of the hydrolytic enzyme substrates described herein in combination with an additional enzyme as described herein, or enzyme co-factor that can be used to detect or quantify the products of hydrolysis of the hydrolytic enzyme substrate by the hydrolytic enzyme, or a reagent for detection of the product of hydrolysis of the hydrolytic enzyme substrate.

Thus in some embodiments, the invention provides a composition that comprises a combination of a hydrolytic enzyme substrate as described above plus at least one of the following:

the hydrolytic enzyme that recognizes and hydrolyzes the hydrolytic enzyme substrate, which enzyme may be present as a conjugate with a recognition element such as an antibody, or it may be present as a polynucleotide sequence that will be expressed as a functional enzyme before detection;

an additional enzyme that can transform the product of Formula (II) that is produced by action of the hydrolytic enzyme on the hydrolytic enzyme substrates of the invention into a new chemical species, often by an oxidation reaction (e.g., an aryl alcohol oxidase, alcohol dehydrogenase, or aryl alcohol dehydrogenase;

a co-factor utilized by the additional enzyme that can help transform the product of Formula (II) that is produced by action of the hydrolytic enzyme on the hydrolytic enzyme substrates of the invention, e.g., NAD+ or NADP+ that can promote oxidation of the compound of Formula II to a carbonyl compound of Formula A-C(=O)—R (II-ox); and a reagent for detecting a by-product formed by the additional enzyme when it transforms the product of Formula (II) into another species, e.g., a reagent for detection of hydrogen peroxide formed upon oxidation of an aryl alcohol of Formula IIB into a carbonyl compound of Formula A-C(=O)—R (II-ox); and/or an enzyme or co-factor that can help transform the carbonyl compound formed by oxidation of the compound of Formula (II) into another species that facilitates detection, e.g., a reducing enzyme as described herein that converts the carbonyl compound back into an alcohol of Formula (II), or a co-factor for such a reducing enzyme.

In some embodiments, the hydrolytic enzyme is not included in these reagent combinations, because for example, the hydrolytic enzyme may be directly linked to the target to be detected. The combination may be prepared to be contacted with a separate sample containing the hydrolytic enzyme. For example, the hydrolytic enzyme can be part of a fusion protein produced from a nucleic acid that encodes a target of interest and also encodes the hydrolytic enzyme. Alternatively, the hydrolytic enzyme may be included in the reagent combinations, and reaction mixtures contacted with the sample will often contain the hydrolytic enzyme, which may be linked or conjugated to a specific recognition moiety such as an antibody directed to the target of interest.

In some embodiments, the invention provides a combination of the hydrolytic enzyme substrate of any of the embodiments described above, and the corresponding hydrolytic enzyme for that particular substrate, i.e., a hydrolytic enzyme that is capable of cleaving the particular hydrolytic enzyme substrate to produce a detectable product of Formula (II). In some embodiments, an aryl alcohol molecule or unsaturated aliphatic alcohol molecule is the product of that hydrolytic cleavage reaction, and the aryl alcohol molecule or unsaturated aliphatic alcohol molecule has a structure of said formula (II):

(II)

wherein A, R and n are as defined for Formula (I).

In some of these embodiments, the hydrolytic enzyme is an esterase, a phosphatase, or a glycosidase. In particular embodiments, the hydrolytic enzyme is selected from the group consisting of an acetylesterase, an amino acid esterase, a carboxylesterase, a nuclease, a phosphodiesterase, a lipase and a phosphatase. For example, the hydrolytic enzyme can be alkaline phosphatase.

In some specific embodiments, the hydrolytic enzyme can be an alkaline phosphatase, an α-amino acid esterase, a galactosidase or a β-glycosidase.

In some of these embodiments, the combination further comprises an oxidizing reagent that is capable of oxidizing the aryl alcohol molecule or unsaturated aliphatic alcohol molecule produced by the cleavage reaction catalyzed by the hydrolytic enzyme. In some such embodiments, the oxidizing reagent is an aryl alcohol oxidase or an alcohol oxidase that is capable of oxidizing the aryl alcohol molecule or unsaturated aliphatic alcohol molecule in the presence of oxygen to produce an aryl aldehyde molecule or unsaturated aliphatic aldehyde molecule (assuming R is H) and $H_2O_2$.

Where an oxidizing reagent is used and $H_2O_2$ can be produced as a by-product of the oxidation reaction, in some embodiments, the combination also comprises a reagent for detecting and/or measuring the $H_2O_2$. Suitable reagents are well known in the art, including those used in Trinder reactions. Thus suitable reagents include a peroxidase such as horseradish peroxidase; a phenol such as phenol; an antipyrine such as 4-aminoantipyrine (4-AA), and/or an aniline analog. Some suitable aniline analogs known for use in these modified Trinder's reactions include ADOS, ADPS, ALPS, DAPS, DAOS, TOOS, MAOS, and MAPS. See, e.g., U.S. Pat. No. 5,156,955 for some suitable Trinder reaction components that can be used in the methods of the invention.

In some embodiments of these combinations, the oxidizing reagent that oxidizes the compound of Formula (II) to a carbonyl compound (aldehydes when R is H; ketone when R is not H) is an aryl alcohol dehydrogenase or an alcohol dehydrogenase that is capable of oxidizing the aryl alcohol molecule or unsaturated aliphatic alcohol molecule in the presence of NAD+ or NADP+ to produce a carbonyl compound and NADH or NADPH. In these embodiments, the combination optionally further comprises NAD+ or NADP+, which acts as a co-factor to promote the oxidation reaction, and is transformed by the oxidation reaction into NADH or NADPH. Optionally in these embodiments, the combination further comprises a reagent for measuring the NADH or NADPH formed by this oxidation reaction.

The combination compositions of the invention include combinations of the hydrolytic enzyme substrate with NADH or NADPH and/or an aryl alcohol dehydrogenase or an alcohol dehydrogenase that is capable of reducing the aryl aldehyde molecule or unsaturated aliphatic aldehyde molecule (compounds of Formula II-ox, where R is H) in the presence of NADH or NADPH. These combinations optionally also include an oxidizing enzyme that can oxidize the initially formed hydrolysis product of Formula II into a carbonyl compound (e.g., Formula II-ox) as described above. Preferably, the oxidizing enzyme is different from the enzymes for reducing the aryl aldehydes or unsaturated aliphatic aldehydes, and preferably the different enzymes do not share the same co-factors. In one preferred embodiment, the oxidizing enzyme is an alcohol oxidase or aryl alcohol oxidase that uses $O_2$ to promote oxidation of the compound of Formula (II), and the reducing enzyme is a dehydrogenase that uses NADH or NADPH to reduce the aldehyde back to an alcohol of Formula II.

Where such complimentary oxidizing and reducing enzymes are employed, a cycling reaction system is formed (see, e.g., FIG. 3), whereby signal amplification can be achieved to greatly increase the sensitivity of the assay system. The cycling assay system can be monitored by measuring hydrogen peroxide formation, by measuring consumption of NADH or NADPH in the reduction reaction, and/or by measuring formation of NAD+ or NADP+ in the reduction reaction. In some embodiments of these compositions, the combination further comprises a reagent for measuring the $H_2O_2$. Suitable reagents for measuring $H_2O_2$ can include at least one of a peroxidase, an antipyrine, a phenol such as 2-chlorophenol, 2,4-dichlorophenol, 4-chlorophenol, 2,6-dichlorophenol, and/or an aniline analog such as DMA, TOOS, TOPS, ADOS, ALOS, ADPS, ALPS, DAPS, DAOS, HDAPS, HDAOS, MAOS, MAPS, or EMAE.

In some embodiments of the foregoing combinations, the hydrolytic enzyme substrate comprises at least a part of a β-glycosidase substrate molecule, and the hydrolytic enzyme is a β-glycosidase. In others, the hydrolytic enzyme substrate comprises a phosphate ester, and the hydrolytic enzyme is alkaline phosphatase. In other embodiments, the hydrolytic enzyme substrate comprises a beta-galactosidic group and the hydrolytic enzyme is beta-galactosidase. In other embodiments, the hydrolytic enzyme substrate is an ester, and the hydrolytic enzyme is an alpha-amino acid esterase, a carboxylesterase, or an acetylesterase.

In some of these compositions, the combination comprises any of the hydrolytic enzyme substrates described herein and at least one of the following:

a) an aryl alcohol oxidase or an aliphatic alcohol oxidase that is capable of oxidizing the aryl alcohol molecule or unsaturated aliphatic alcohol molecule in the presence of oxygen to produce an aryl aldehyde molecule or unsaturated aliphatic aldehyde molecule and $H_2O_2$; and/or b) NADH or NADPH; and/or c) an aryl alcohol dehydrogenase or an alcohol dehydrogenase that is capable of reducing the aryl aldehyde molecule or unsaturated aliphatic aldehyde molecule in the presence of NADH or NADPH; and/or d) a reagent for measuring $H_2O_2$.

In another aspect, the invention provides kits for determining and/or quantifying the amount of a hydrolytic enzyme, which include any of the compounds described herein as suitable hydrolytic enzyme substrates for purposes of the invention and optionally any of the combination compositions described above. In some embodiments, any one of the combinations set forth above is provided in the form of a kit. The kit can include the components of the combination packaged separately, or it can include mixtures of the components of an embodiment of the combinations premixed in a single container, where the components are compatible for mixing. The kit may further comprise one or more standards useful for calibration of the assay system, and instructions for performing an assay with the hydrolytic enzyme substrate or combination composition.

Any of the foregoing combinations can be comprised in an assay, isolation and/or production system for a target to be produced or detected. The target is an analyte to be detected or quantified, or a product to be produced and detected or quantified, and the combinations and kits described above can include a moiety that is specific for the target, such as a PCR primer or an antibody. In some embodiments, the target is an inorganic molecule, an organic molecule and/or a complex thereof. In some embodiments, the target is an organic molecule selected from the group consisting of an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

Any suitable alcohol oxidase can be used in the present combinations. For example, the alcohol oxidase disclosed and/or claimed U.S. Pat. Nos. 7,160,708, 5,166,329, 4,956,290, 4,729,956 and 4,619,898 can be used. In another example, the alcohol oxidase disclosed in Janssen and Ruelius, *Biochim. Biophys. Acta.*, 151(2): 330-42 (1968), and Suye, *Curr. Microbiol.*, 34(6): 374-7 (1997) can be used.

Any suitable aryl alcohol oxidase can be used in the present combinations. For example, the aryl alcohol oxidase disclosed and/or claimed in U.S. Pat. Nos. 3,183,235, 3,290,326 and 6,835,212, and U.S. patent application US2009/053780 A1 can be used. In another example, the aryl alcohol oxidase disclosed in Farmer et al., *Biochem. J.* 74:257-62 (1960) and Guillen and Evans, *Applied and Environmental Microbiology*, 60(8):2811-2817 (1994) can be used.

Any suitable aryl alcohol dehydrogenase can be used in the present combinations. For example, the aryl alcohol dehydrogenase disclosed and/or claimed in U.S. Pat. Nos. 4,020,070, 5,182,209, 6,262,295, 7,750,135, and U.S. patent application US2009/017510 A1, US2009/186900 A1, US2006/074060 A1, and JP2147956 A can be used. In another example, the aryl alcohol dehydrogenase disclosed in Suhara et al., *Arch. Biochem. Biophys.*, 130(1): 422-9 (1969), and Yamanaka and Minoshima, *Agric. Biol. Chem.*, 48:1161-1171 (1984) can be used.

Any suitable alcohol dehydrogenase can be used in the present combinations. For example, the alcohol dehydrogenase disclosed and/or claimed in U.S. Pat. Nos. 7,750,135, 7,354,751, 6,552,249, 6,432,688, 6,255,092, 6,225,099, 5,908,924, 5,855,881, 5,695,973, 5,445,943, 5,385,833, 5,344,777, 5,162,516, 5,162,203, 4,241,184, 4,131,727, and 4,111,751 can be used. In another example, the alcohol dehydrogenase disclosed in Yakushi and Matsushita, *Appl Microbiol Biotechnol.*, 86(5):1257-65 (2010) and Yin, Alcohol Alcohol Suppl., 2:113-9 (1994) can be used.

The combinations of the invention can be embodied in a system such as a system for immunoassay, protein sequencing, nucleic acid amplification, hybridization or sequencing.

Exemplary immunoassays include sandwich or competitive assay, enzyme-linked immunosorbent assay (ELISA), immunoblotting, immunoprecipitation, immunostaining, lateral flow immunoassay, u-capture assay, inhibition assay and avidity assay. Exemplary nucleic acid sequencing technologies include DNA sequencing technology using a hydrolytic enzyme, e.g., an alkaline phosphatase, to generate a signal readout. See e.g., Patel and Nash, *Biotechniques*, 18(2):328-33 (1995).

The combinations of the invention can be used in any suitable assay formats or configurations. In some embodiments, the combinations of the invention can be used in heterogeneous assay formats. In other embodiments, the combinations of the invention can be used in homogeneous assay formats. Exemplary homogeneous assay formats include cloned enzyme donor immunoassay (CEDIA), multiplied immunoassay techniques (EMIT), apoenzyme reactivation immunoassay (ARIA), cofactor-labeled immunoassay and inhibitor-labeled immunoassay. See e.g., U.S. Pat. Nos. 4,708,929, 5,120,653, 5,244,785, and 5,362,625, WO 96/41172 A1, and Jenkins, *J. Immunol. Meth.*, 150:91-97 (1992).

E. METHODS OF USING THE HYDROLYTIC ENZYME SUBSTRATES

In another aspect, the invention provides for methods for using the hydrolytic enzyme substrates and/or combinations described above to detect the presence or amount of the hydrolytic enzyme in a sample, which in some embodiments is used to detect the presence or amount of a target molecule in the sample. The target molecule may be conjugated with the hydrolytic enzyme where the enzyme functions as a label, for example; or the hydrolytic enzyme may be attached or conjugated to a binding moiety that is specific for the target molecule, e.g., an antibody that specifically recognizes and binds to the target molecule, or to a complex of the target molecule with another moiety such as another enzyme as part of a sandwich assay. In some embodiments, the hydrolytic enzyme itself may be the species to be detected or quantified.

The hydrolytic enzyme will typically be in a sample, which can be any suitable composition. Frequently it will be a solution or suspension, primarily aqueous, and containing suitable buffering agents to maintain an appropriate pH for the hydrolytic enzyme to function. Selection of suitable temperature, pH, and concentration and other parameters are within the ordinary level of skill for a given hydrolytic enzyme.

In some embodiments, the invention provides a method for assessing activity and/or amount of a hydrolytic enzyme in a sample, which method comprises:

a) contacting a sample containing or suspected of containing a hydrolytic enzyme with a hydrolytic enzyme substrate having a structure of formula (I):

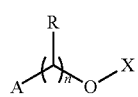
(I)

under conditions where said hydrolytic enzyme, if present in said sample, cleaves said substrate to produce an aryl alcohol molecule or unsaturated aliphatic alcohol molecule having a structure of formula (II) and a compound having a structure of formula (III):

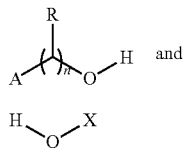

wherein A, R, n and X are as defined above for Formula (I); and b) assessing the presence and/or amount of said aryl alcohol molecule or unsaturated aliphatic alcohol molecule to assess activity and/or amount of said hydrolytic enzyme in said sample.

The amount or presence of the aryl alcohol or unsaturated aliphatic alcohol can be assessed directly or indirectly, by any convenient method. In some embodiments, the presence or amount of the alcohol is detected by converting it into a carbonyl compound as described herein, typically by an enzymatic oxidation. The oxidation can be accomplished with various enzymes as described herein (e.g., aryl alcohol oxidase; alcohol dehydrogenase; aryl alcohol dehydrogenase). The hydrolytic enzyme substrate can be any of those described above, provided it is selected to be compatible with the hydrolytic enzyme to be detected and thus contains a recognition moiety specific for that hydrolytic enzyme, and is capable of being hydrolyzed by that hydrolytic enzyme.

The method is thus an assay that involves contacting the sample with the hydrolytic enzyme substrate, either alone or in any of the combinations described above. The conditions for the assay are selected such that the hydrolytic enzyme, if present, will hydrolyze the hydrolytic enzyme substrate to produce products as discussed above. Typically, an excess amount of the hydrolytic enzyme substrate will be included relative to the amount of enzyme likely to be present, so the amount of product can exceed the amount of enzyme, thus enhancing the effective signal strength and making assay more sensitive, and giving a substantially linear rate of product formation.

It will be understood that the assays described herein can be quantitative or qualitative. Qualitatively, one can detect the product formed to verify that the hydrolytic enzyme is present, often by convenient color-change or spectrophotometric assays that confirm some product has formed. Where a quantitative result is desired, it will frequently be necessary to test one or more standards in order to interpret the data from the assay, which will typically reflect the rate of formation of the products rather than directly describing the amount of enzyme. It is thus often necessary to test with the assay, in addition to the test sample, at least one and optionally more than one standard sample having a known amount of the hydrolytic enzyme in order to determine the amount of hydrolytic enzyme present from the data on rate of product formation. Such calibration methods are well known to those of ordinary skill in the art.

In some embodiments of these methods, the hydrolytic enzyme is an esterase, or a glycosidase. In some embodiments, the hydrolytic enzyme is an esterase selected from the group consisting of an acetylesterase, an amino acid esterase, and a carboxylesterase; in some embodiments, the enzyme is a nuclease, a phosphodiesterase, a lipase or a phosphatase. In some particular embodiments, the hydrolytic enzyme is an alkaline phosphatase. In other particular embodiments, the hydrolytic enzyme is an α-amino acid esterase; or a β-glycosidase.

In some embodiments of these methods, the step of assessing the presence and/or amount of the aryl alcohol molecule or unsaturated aliphatic alcohol molecule comprises oxidizing the aryl alcohol molecule or unsaturated aliphatic alcohol molecule with an oxidizing reagent. Where R is H, the oxidation product is an aldehyde; where R is alkyl or aryl, the oxidation product is a ketone. In some preferred embodiments, n is 1 and R is H, so the product of the oxidation is an aldehydes of formula A-CHO, where A is as described for formula (I).

In some of these embodiments, the presence and/or amount of the aryl alcohol molecule or unsaturated aliphatic alcohol molecule is assessed by oxidizing the aryl alcohol molecule or unsaturated aliphatic alcohol molecule with an aryl alcohol oxidase or an aliphatic alcohol oxidase in the presence of oxygen to produce $H_2O_2$ and assessing the presence and/or amount of the $H_2O_2$. Methods for assessing the presence or amount of hydrogen peroxide are well known in the art, and include variations of the Trinder reaction. In some such embodiments, a reagent comprising at least one of a peroxidase, a phenol, an antipyrine, and/or an aniline analog is used to detect the presence and/or amount of the $H_2O_2$. Suitable reagents are discussed, for example, in U.S. Pat. No. 5,156,955.

In alternative methods, the presence and/or amount of the aryl alcohol molecule or unsaturated aliphatic alcohol molecule is assessed by oxidizing the aryl alcohol molecule or unsaturated aliphatic alcohol molecule with an aryl alcohol dehydrogenase or an alcohol dehydrogenase in the presence of $NAD^+$ or $NADP^+$ to produce NADH or NADPH, and assessing the presence and/or amount of the NAD+, NADP+, NADH or NADPH. Methods to monitor reactions using NAD+/NADH or NADP+/NADPH are well known in the art, and are conveniently applied to these assay methods.

In some embodiments, the presence and/or amount of the aryl alcohol molecule or unsaturated aliphatic alcohol molecule is assessed by:

a) oxidizing the aryl alcohol molecule or unsaturated aliphatic alcohol molecule with an aryl alcohol oxidase or an aliphatic alcohol oxidase in the presence of oxygen to produce aryl aldehyde molecule or unsaturated aliphatic aldehyde molecule and $H_2O_2$;

b) reducing the aryl aldehyde molecule or unsaturated aliphatic aldehyde molecule with an aryl alcohol dehydrogenase or an alcohol dehydrogenase in the presence of NADH or NADPH to form a reaction cycle in which the reduced aryl alcohol molecule or unsaturated aliphatic alcohol molecule is oxidized by the aryl alcohol oxidase or an aliphatic alcohol oxidase in the presence of oxygen to produce additional aryl aldehyde molecule or unsaturated aliphatic aldehyde molecule and $H_2O_2$; and c) assessing the presence and/or amount of the $H_2O_2$, or the amount of NADH, NADPH, NAD+, or NADP+.

In these embodiments, two different enzymes are used, one to oxidize alcohol to aldehydes, and another to reduce aldehydes back to alcohol. The different enzymes use different co-factors and produce different by-products; and the combination of the two different enzymes operating simultaneously provides a cycling assay system that results in effective amplification of the signal from the initial hydrolysis of the hydrolytic enzyme substrate. The amount of by-products formed from the cycling oxidation/reduction combination can far exceed the amount of hydrolytic enzyme substrate used. This system thus introduces two amplification steps, the initial amplification from amount of enzyme to the amount of hydrolyzed substrate; and the further amplification provided by cycling the hydrolyzed substrate molecule between oxidized and reduced states.

The amount or presence of $H_2O_2$ can be measured by known methods such as the Trinder reactions as discussed above, as can the amounts of the co-factors present. It is also possible in these methods to monitor both hydrogen peroxide formation and the rate of the NAD+/NADH or NADP+/NADH formation.

In some embodiments of these methods, the hydrolytic enzyme substrate comprises at least a part of (a recognition moiety of) a β-glycosidase substrate molecule, and the hydrolytic enzyme is a β-glycosidase.

In other embodiments, the hydrolytic enzyme substrate comprises at least a part of an alkaline phosphatase substrate molecule (e.g., an optionally substituted benzyl phosphate), and the hydrolytic enzyme is an alkaline phosphatase.

The methods described herein can be used as an analytical assay to detect the presence of a target or as part of an isolation method for a target; or as part of a process for production of a target molecule. The target molecule can be organic or inorganic or a complex, as described above. In some embodiments, the target is an organic molecule selected from the group consisting of an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

In some embodiments, the methods are utilized in an immunoassay, protein sequencing, nucleic acid amplification, hybridization or sequencing. In some embodiments, the methods are used in an RNA or DNA sequencing system. In these embodiments, alkaline phosphatase is a preferred hydrolytic enzyme.

Any suitable alcohol oxidase can be used in the present methods. For example, the alcohol oxidase disclosed and/or claimed U.S. Pat. Nos. 7,160,708, 5,166,329, 4,956,290, 4,729,956 and 4,619,898 can be used. In another example, the alcohol oxidase disclosed in Janssen and Ruelius, *Biochim. Biophys. Acta.*, 151(2): 330-42 (1968), and Suye, *Curr. Microbiol.*, 34(6): 374-7 (1997) can be used.

Any suitable aryl alcohol oxidase can be used in the present methods. For example, the aryl alcohol oxidase disclosed and/or claimed in U.S. Pat. Nos. 3,183,235, 3,290,326 and 6,835,212, and U.S. patent application US2009/053780 A1 can be used. In another example, the aryl alcohol oxidase disclosed in Farmer et al., *Biochem. J.* 74:257-62 (1960) and Guillen and Evans, *Applied and Environmental Microbiology*, 60(8):2811-2817 (1994) can be used.

Any suitable aryl alcohol dehydrogenase can be used in the present methods. For example, the aryl alcohol dehydrogenase disclosed and/or claimed in U.S. Pat. Nos. 4,020,070, 5,182,209, 6,262,295, 7,750,135, and U.S. patent application US2009/017510 A1, US2009/186900 A1, US2006/074060 A1, and JP2147956 A can be used. In another example, the aryl alcohol dehydrogenase disclosed in Suhara et al., *Arch. Biochem. Biophys.*, 130(1): 422-9 (1969), and Yamanaka and Minoshima, *Agric. Biol. Chem.*, 48:1161-1171 (1984) can be used.

Any suitable alcohol dehydrogenase can be used in the present methods. For example, the alcohol dehydrogenase disclosed and/or claimed in U.S. Pat. Nos. 7,750,135, 7,354, 751, 6,552,249, 6,432,688, 6,255,092, 6,225,099, 5,908,924, 5,855,881, 5,695,973, 5,445,943, 5,385,833, 5,344,777, 5,162,516, 5,162,203, 4,241,184, 4,131,727, and 4,111,751 can be used. In another example, the alcohol dehydrogenase disclosed in Yakushi and Matsushita, *Appl Microbiol Biotechnol.*, 86(5):1257-65 (2010) and Yin, Alcohol Alcohol Suppl., 2:113-9 (1994) can be used.

The present methods can be used in any suitable assays such as immunoassay, protein sequencing, nucleic acid amplification, hybridization or sequencing. Exemplary immunoassays include sandwich or competitive assay, enzyme-linked immunosorbent assay (ELISA), immunoblotting, immunoprecipitation, immunostaining, lateral flow immunoassay, u-capture assay, inhibition assay and avidity assay. Exemplary nucleic acid sequencing technologies include DNA sequencing technology using a hydrolytic enzyme, e.g., an alkaline phosphatase, to generate a signal readout. See e.g., Patel and Nash, *Biotechniques,* 18(2):328-33 (1995).

The present methods can be used in any suitable assay formats or configurations. In some embodiments, the present methods can be used in heterogeneous assay formats. In other embodiments, the present methods can be used in homogeneous assay formats. Exemplary homogeneous assay formats include cloned enzyme donor immunoassay (CEDIA), multiplied immunoassay techniques (EMIT), apoenzyme reactivation immunoassay (ARIA), cofactor-labeled immunoassay and inhibitor-labeled immunoassay. See e.g., U.S. Pat. Nos. 4,708,929, 5,120,653, 5,244,785, and 5,362,625, WO 96/41172 A1, and Jenkins, *J. Immunol. Meth.,* 150:91-97 (1992).

The present combinations and/or methods can be used to detect an analyte in any suitable sample liquid. In some embodiments, the liquid sample can be body fluid sample, such as a whole blood, a serum, a plasma, a urine sample or an oral fluid. Such body fluid sample can be sued directly or can be processed, e.g., enriched, purified, or diluted, before use. In other embodiments, the liquid sample can be a liquid extract, suspension or solution derived from a solid or semi-solid biological material such as a phage, a virus, a bacterial cell, an eukaryotic cell, a fugal cell, a mammalian cell, a cultured cell, a cellular or subcellular structure, cell aggregates, tissue or organs. In specific embodiments, the sample liquid is obtained or derived from a mammalian or human source. In still other embodiments, the liquid sample is a sample derived from a biological, a forensics, a food, a biowarfare, or an environmental source. In other embodiments, the sample liquid is a clinical sample, e.g., a human or animal clinical sample. In still other embodiments, the sample liquid is a man-made sample, e.g., a standard sample for quality control or calibration purposes.

The present combinations and/or methods can be used to detect the presence, absence and/or amount of an analyte in any suitable sample liquid. In some embodiments, the present test devices are used to detect the presence or absence of an analyte in any suitable sample liquid, i.e., to provide a yes or no answer. In other embodiments, the present test devices are used to quantify or semi-quantify the amount of an analyte in a liquid sample.

The combinations and/or methods can be used to detect the presence, absence and/or amount of a single analyte in any suitable sample liquid. Alternatively, the present test devices can be used to detect the presence, absence and/or amount of multiple analytes in a liquid sample. In still other embodiments, the present test devices can be used to quantify or semi-quantify the amounts of the multiple analytes in the liquid sample.

The combinations and/or methods can be used to detect the presence, absence and/or amount of any suitable analyte in a sample liquid. Exemplary analytes include inorganic molecules, organic molecules or complexes thereof. Exemplary organic molecules can be an amino acid, a peptide, a protein, a nucleoside, a nucleotide, an oligonucleotide, a nucleic acid, e.g., a DNA or RNA molecule or a hybrid thereof, a vitamin, a monosaccharide, an oligosaccharide, a carbohydrate, a lipid and a complex thereof. In some embodiments, the analyte is a cell, a virus or a molecule. In other embodiments, the analyte is a disease or disorder marker, an antigen of an infectious organism, an antibody to an infectious organism, etc.

The combinations and/or methods can be used for any suitable purpose. For example, present combinations and/or methods can be used for clinical diagnosis, prognosis, risk assessment and prediction, stratification and treatment monitoring and adjustment. In another example, present combinations and/or methods can be used for various research purposes, such as basic research, drug candidate screening, animal studies, and clinical trials. In still another example, present combinations and/or methods can be used in tests for standard setting, quality control, illegal drug screening, food safety, environmental safety, industrial safety, and pollution, etc. The present combinations and/or methods can be used in any suitable settings, such as tests in the labs, clinics, hospitals, physician's offices, homes, natural environments and battle fields.

F. EXEMPLARY EMBODIMENTS

Hydrolytic enzymes are widely used in bioassays for research and clinical diagnostics. Two of the most commonly used hydrolytic enzymes in bioassays are beta-galactosidase and alkaline phosphatase. Beta-galactosidase is often used as the enzyme for the CEDIA (cloned enzyme donor immunoassay) platform (See, e.g., U.S. Pat. Nos. 4,708,929, 5,120,653, 5,244,785, and 5,362,625, and WO 96/41172 A1) which is widely used in many assays such as clinical diagnostics for detecting various analytes including hormones, vitamins, therapeutic drugs and tests for drug-of-abuse.

In the CEDIA assay, two fragments of beta-galactosidase (EC 3.2. 1. 23), typically prepared by recombinant DNA technology, are used. The larger fragment is referred as enzyme acceptor or EA, and the smaller fragment is referred as enzyme donor or ED. Both fragments are enzymatically inactive when they are separated. When these fragments are mixed in solution, they spontaneously assemble into a fully active enzyme like a native beta-galactosidase. In many assays including clinical diagnostics, homogeneous assays are desirable because they save time, save reagents, and are easy to automate. Homogeneous assays allow a simple "mix and read" process, without requiring lengthy, time consuming wash steps to remove unbound constituents.

CEDIA assay is a homogenous assay that meets some of the desired clinical testing requirements. The CEDIA homogenous assay platform operates by controlling the spontaneous assembly of the EA and ED through target-binder, e.g., an antigen-antibody, reaction. In some embodiments, an analyte or biomarker can be covalently attached to the ED in a way such that there is no interference in forming active beta-galactosidase enzyme when the ED conjugate is mixed with EA. Adding to the system a binder or an antibody to the analyte or the biomarker will inhibit the spontaneous assembly of enzyme. Placing this system in competition for an analyte in a sample, e.g., a patient's serum, will create active enzyme in direct proportion to the amount of free unknown analyte or biomarker in the sample. The amount of enzyme created is monitored through the hydrolysis of an appropriate enzyme substrate such as o-nitrophenyl-beta-D-galactopyranoside or chlorophenol red-beta-D-galactopyranoside. However, these substrates have limitations in their extinction coefficients, and are not suitable to make the CEDIA assay a highly sensitive assay system similar to the chemiluminescent based heterogenous immunoassay.

In some embodiments, to improve the CEIDA system, we have designed a series of new substrates for beta-galactosidase. One distinctive characteristic of the new substrates is the linkage of an aryl alcohol molecule through its hydroxyl group to a beta-D-galactopyranoside. Hydrolysis of these substrates by beta-galactosidase generates free aryl alcohol molecules which are oxidized to aryl aldehyde by aryl alcohol oxidase with the concomitant formation of a hydrogen peroxide ($H_2O_2$). Aryl aldehyde is then reduced back to aryl alcohol by an enzyme aryl alcohol dehydrogenase or alcohol dehydrogenase. This oxidation and reduction reactions form an enzyme cycling with an accumulation of a reaction by-product $H_2O_2$ which is exponentially amplified in each reaction cycle.

Any suitable aryl alcohol oxidase and aryl alcohol dehydrogenase can be used. For example, the aryl alcohol oxidase and aryl alcohol dehydrogenase from a fungus, e.g., *Pleurotus eryngii*, can be used (Guillen and Evans, *Applied and Environmental Microbiology*, 60(8):2811-2817 (1994)). Use of the novel substrate for beta-galactosidase in the presently described assays allows for a coupled enzyme cycling reaction which significantly amplifies the reaction signal for detection, and thus improving the assay sensitivity of the CEDIA homogenous platform.

As another example, alkaline phosphatase is an enzyme that is widely used as a reporting enzyme in various assays including immunoassays such as ELISA, and DNA sequencing. The new substrates described herein include aryl alcohol analogs linking the hydroxyl group with a phosphate group ($H_2PO_4$). Hydrolysis of these substrates by an alkaline phosphatase will generate free aryl alcohol molecules which will serve as substrate for aryl alcohol oxidase and can be coupled to the aryl alcohol oxidase/dehydrogenase based enzyme cycling system for signal amplification. This will give a more sensitive detection for immunoassays and DNA sequencing.

The following enumerated embodiments represent certain aspects of the invention:

1. A hydrolytic enzyme substrate, which is a compound of formula (I):

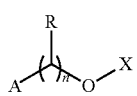
(I)

wherein:

A is an aromatic or heteroaromatic group, a 1-alkene or a 1-alkyne, each of which is optionally substituted;

each R is independently H or an optionally substituted C1-C4 alkyl or aryl;

n is an integer from 1-4;

and X is a group comprising a substrate moiety, wherein the substrate moiety comprises a recognition component of a substrate for the hydrolytic enzyme, and wherein the activity of said hydrolytic enzyme is capable of hydrolyzing said compound of formula (I) to form compounds (II) and (III):

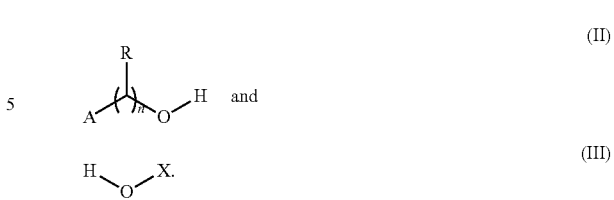

2. The hydrolytic enzyme substrate of embodiment 1, wherein A is an optionally substituted aromatic or heteroaromatic group.

3. The hydrolytic enzyme substrate of embodiment 2, wherein A is optionally substituted phenyl or naphthyl.

4. The hydrolytic enzyme substrate of claim 1, wherein A is a 1-alkene of the

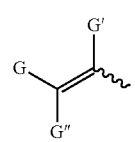

wherein the wavy line indicates the point of attachment of A to —[CH(R)]$_n$—O—X in Formula (I), and each G, G' and G" is independently H or an optionally substituted group selected from the group consisting of C1-C8 alkyl, C2-C8 alkenyl, C2-C8 alkynyl, C3-C8 cycloalkyl, C3-C8 heterocycloalkyl, aryl, and heteroaryl.

5. The hydrolytic enzyme substrate of embodiment 1, wherein A is a 1-alkyne of the formula (V):

wherein the wavy line indicates the point of attachment of A to —[CH(R)]$_n$—O—X in Formula (I), and G is H or an optionally substituted member selected from the group consisting of C1-C8 alkyl, C2-C8 alkenyl, C2-C8 alkynyl, C3-C8 cycloalkyl, C3-C8 heterocycloalkyl, aryl, and heteroaryl.

6. The hydrolytic enzyme substrate of embodiment 1, wherein R is H, Me or phenyl.

7. The hydrolytic enzyme substrate of embodiment 1, wherein X comprises a saccharide.

8. The hydrolytic enzyme substrate of embodiment 7, wherein the compound is of the formula (VIa) or (VIb):

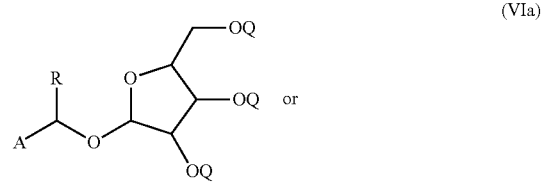
(VIa)

-continued

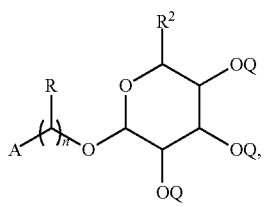
(VIb)

wherein $R^2$ is H or —$CH_2OQ$, and each Q is independently H or a monosaccharide, disaccharide or oligosaccharide, and A, R and n are as defined in claim 1.

9. The hydrolytic enzyme substrate of embodiment 1, wherein the compound is an ester of formula (VII):

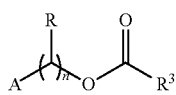
(VII)

wherein $R^3$ is H or an optionally substituted aryl, heteroaryl, C1-C8 alkyl, C3-C8 cycloalkyl, or C3-C8 heterocyclyl group, and A, R and n are as defined in claim 1.

10. The hydrolytic enzyme substrate of embodiment 9, wherein $R^3$ is selected from the group consisting of Me, Et, and phenyl, or wherein $HO_2C$—$R^3$ is an alpha-amino acid.

11. The hydrolytic enzyme substrate of embodiment 1, wherein the compound is of

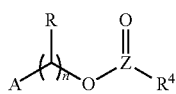
(VII)

wherein Z is N, S, S=O, P, or P—OH, and $R^4$ is O, hydroxy, C1-C4 alkoxy, C1-C4 alkyl, or aryl.

12. The hydrolytic enzyme substrate of embodiment 1, wherein X comprises a phosphate group.

13. The hydrolytic enzyme substrate of embodiment 12, wherein the compound is of

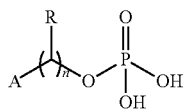

or a salt thereof.

14. The hydrolytic enzyme substrate of any of embodiments 1-3 or 6-13, wherein A is an optionally substituted phenyl group.

15. The hydrolytic enzyme substrate of embodiment 14, wherein the phenyl group is unsubstituted, or is substituted with 1-3 groups selected from halo, hydroxy, CN, $NO_2$, COOR', $CONR'_2$, $NR'_2$, OR', optionally substituted C1-4 alkyl, SR', $SO_2R'$, or $SO_2NR'_2$, wherein each R' is independently H or optionally substituted C1-4 alkyl, and two R' on the same or adjacent atoms can be taken together to form an optionally substituted C3-C8 heterocyclic ring.

16. The hydrolytic enzyme substrate of any of the preceding embodiments, wherein optional substituents for alkyl and heterocyclic groups are selected from halo, oxo, CN, $NO_2$, COOR'', $CONR''_2$, $NR''_2$, OR'', optionally substituted C1-4 alkyl, SR', $SO_2R''$, or $SO_2NR''_2$, wherein each R'' is independently H or C1-4 alkyl.

17. The hydrolytic enzyme substrate of embodiment 1, wherein A is a group of the formula (X):

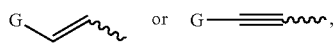

wherein the wavy line indicates the point of attachment of A to —$[CH(R)]_n$—O—X in Formula (I), and each G is independently H or an optionally substituted group selected from the group consisting of C1-C8 alkyl, C2-C8 alkenyl, C2-C8 alkynyl, C3-C8 cycloalkyl, C3-C8 heterocycloalkyl, aryl, and heteroaryl.

18. The hydrolytic enzyme substrate of any of the preceding embodiments, wherein R is H.

19. The hydrolytic enzyme substrate of any of the preceding embodiments, wherein n is 1.

20. The hydrolytic enzyme substrate of embodiment 1, wherein X comprises a substrate moiety for a glycosidase.

21. The hydrolytic enzyme substrate of embodiment 20, wherein the glycosidase is a beta-galactosidase.

22. The hydrolytic enzyme substrate of embodiment 1, wherein X comprises a substrate moiety for an esterase.

23. The hydrolytic enzyme substrate of embodiment 22, wherein the esterase is selected from the group consisting of a carboxylesterase, an acetyl esterase and an alpha-amino acid esterase.

24. The hydrolytic enzyme substrate of embodiment 1, wherein X comprises a substrate moiety for a phosphatase.

25. The hydrolytic enzyme substrate of embodiment 24, wherein the phosphatase is an alkaline phosphatase.

26. A combination, which comprises:
a) a hydrolytic enzyme substrate of any of the embodiments 1-25; and
b) a hydrolytic enzyme that is capable of cleaving said hydrolytic enzyme substrate to produce an aryl alcohol molecule or unsaturated aliphatic alcohol molecule as a product of said cleavage reaction catalyzed by said hydrolytic enzyme, wherein said aryl alcohol molecule or unsaturated aliphatic alcohol molecule has a structure of said formula (II):

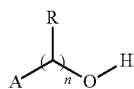
(II)

wherein A, R and n are as defined in claim 1.

27. The combination of embodiment 26, wherein the hydrolytic enzyme is an esterase, a phosphatase, or a glycosidase.

28. The combination of embodiment 27, wherein the hydrolytic enzyme is selected from the group consisting of an acetylesterase, an amino acid esterase, a carboxylesterase, a nuclease, a phosphodiesterase, a lipase and a phosphatase.

29. The combination of embodiment 27, wherein the hydrolytic enzyme is an alkaline phosphatase.

30. The combination of embodiment 28, wherein the hydrolytic enzyme is an α-amino acid esterase.

31. The combination of embodiment 27, wherein the hydrolytic enzyme is a beta-galactosidase.

32. The combination of embodiment 27, wherein the hydrolytic enzyme is a β-glycosidase.

33. The combination of embodiment 26, which further comprises an oxidizing reagent that is capable of oxidizing the aryl alcohol molecule or unsaturated aliphatic alcohol molecule produced by the cleavage reaction catalyzed by the hydrolytic enzyme.

34. The combination of embodiment 33, wherein the oxidizing reagent is an aryl alcohol oxidase or an aliphatic alcohol oxidase that is capable of oxidizing the aryl alcohol molecule or unsaturated aliphatic alcohol molecule in the presence of oxygen to produce an aryl aldehyde molecule or unsaturated aliphatic aldehyde molecule and $H_2O_2$.

35. The combination of embodiment 34, which further comprises a reagent for measuring the $H_2O_2$.

36. The combination of embodiment 35, wherein the reagent for measuring the $H_2O_2$ comprises a peroxidase, 4-AA and/or an aniline analog.

37. The combination of embodiment 33, wherein the oxidizing reagent is an aryl alcohol dehydrogenase or an alcohol dehydrogenase that is capable of oxidizing the aryl alcohol molecule or unsaturated aliphatic alcohol molecule in the presence of $NAD^+$ or $NADP^+$ to produce NADH or NADPH.

38. The combination of embodiment 37, which further comprises $NAD^+$ or $NADP^+$.

39. The combination of embodiment 38, which further comprises a reagent for measuring the NADH or NADPH.

40. The combination of embodiment 34, which further comprises NADH or NADPH and an aryl alcohol dehydrogenase or an alcohol dehydrogenase that is capable of reducing the aryl aldehyde molecule or unsaturated aliphatic aldehyde molecule in the presence of NADH or NADPH.

41. The combination of embodiment 40, which further comprises a reagent for measuring the $H_2O_2$.

42. The combination of embodiment 41, wherein the reagent for measuring the $H_2O_2$ comprises at least one of a peroxidase, an antipyrine, a phenol, and/or an aniline analog.

43. The combination of embodiment 26, wherein the hydrolytic enzyme substrate comprises at least a part of a β-glycosidase substrate molecule, and the hydrolytic enzyme is a β-glycosidase or beta-galactosidase.

44. The combination of embodiment 43, which further comprises:
a) an aryl alcohol oxidase or an aliphatic alcohol oxidase that is capable of oxidizing the aryl alcohol molecule or unsaturated aliphatic alcohol molecule in the presence of oxygen to produce an aryl aldehyde molecule or unsaturated aliphatic aldehyde molecule and $H_2O_2$;
b) NADH or NADPH;
c) an aryl alcohol dehydrogenase or an alcohol dehydrogenase that is capable of reducing the aryl aldehyde molecule or unsaturated aliphatic aldehyde molecule in the presence of NADH or NADPH.

45. The combination of embodiment 44, which further comprises a reagent for measuring $H_2O_2$.

46. The combination of embodiment 26, wherein the hydrolytic enzyme substrate comprises at least a part of an alkaline phosphatase substrate molecule, and the hydrolytic enzyme is an alkaline phosphatase.

47. The combination of embodiment 46, which further comprises:
a) an aryl alcohol oxidase or an aliphatic alcohol oxidase that is capable of oxidizing the aryl alcohol molecule or unsaturated aliphatic alcohol molecule in the presence of oxygen to produce oxidized aryl alcohol molecule or unsaturated aliphatic alcohol molecule and $H_2O_2$;
b) NADH or NADPH;
c) an aryl alcohol dehydrogenase or an alcohol dehydrogenase that is capable of reducing the oxidized aryl alcohol molecule or unsaturated aliphatic alcohol molecule in the presence of NADH or NADPH.

48. The combination of embodiment 47, which further comprises at least one reagent for measuring $H_2O_2$.

49. The combination of any of the embodiments 26-48, wherein the components of the combination are comprised in a kit.

50. The combination of any of the embodiments 26-49, which combination is comprised in an assay, isolation and/or production system for a target.

51. The combination of embodiment 50, wherein the target is an inorganic molecule, an organic molecule and/or a complex thereof.

52. The combination of embodiment 51, wherein the target is an organic molecule selected from the group consisting of an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

53. The combination of embodiment 52, wherein the system is a system for immunoassay, protein sequencing, nucleic acid amplification, hybridization and/or sequencing.

54. A method for assessing activity and/or amount of a hydrolytic enzyme in a sample, which method comprises:
a) contacting a hydrolytic enzyme substrate of any of the embodiments 1-25 with a sample containing or suspected of containing a hydrolytic enzyme with a hydrolytic enzyme substrate having a structure of formula (I):

under conditions where said hydrolytic enzyme, if present in said sample, cleaves said substrate to produce an aryl alcohol molecule or unsaturated aliphatic alcohol molecule having a structure of formula (II) and a compound having a structure of formula (III):

wherein A, R, n and X are as defined in claim 1; and
b) assessing the presence and/or amount of said aryl alcohol molecule or unsaturated aliphatic alcohol molecule to assess activity and/or amount of said hydrolytic enzyme in said sample.

55. The method of embodiment 54, wherein the hydrolytic enzyme is an esterase, a beta-galactosidase, or a glycosidase.

56. The method of embodiment 55, wherein the hydrolytic enzyme is an esterase selected from the group consisting of an acetylesterase, an amino acid esterase, a carboxylesterase, a nuclease, a phosphodiesterase, a lipase and a phosphatase.

57. The method of embodiment 56, wherein the hydrolytic enzyme is an alkaline phosphatase.

58. The method of embodiment 56, wherein the hydrolytic enzyme is an α-amino acid esterase.

59. The method of embodiment 55, wherein the hydrolytic enzyme is a beta-galactosidase.

60. The method of embodiment 55, wherein the hydrolytic enzyme is a β-glycosidase.

61. The method of embodiment 54, wherein the step of assessing the presence and/or amount of the aryl alcohol molecule or unsaturated aliphatic alcohol molecule comprises oxidizing the aryl alcohol molecule or unsaturated aliphatic alcohol molecule with an oxidizing reagent.

62. The method of embodiment 61, wherein the presence and/or amount of the aryl alcohol molecule or unsaturated aliphatic alcohol molecule is assessed by oxidizing the aryl alcohol molecule or unsaturated aliphatic alcohol molecule with an aryl alcohol oxidase or an aliphatic alcohol oxidase in the presence of oxygen to produce $H_2O_2$ and assessing the presence and/or amount of the $H_2O_2$.

63. The method of embodiment 62, wherein the presence and/or amount of the $H_2O_2$ is assessed by contacting the $H_2O_2$ with a peroxidase, a phenol, an antipyrine, and/or an aniline analog.

64. The method of embodiment 54, wherein the presence and/or amount of the aryl alcohol molecule or unsaturated aliphatic alcohol molecule is assessed by oxidizing the aryl alcohol molecule or unsaturated aliphatic alcohol molecule with an aryl alcohol dehydrogenase or an alcohol dehydrogenase in the presence of $NAD^+$ or $NADP^+$ to produce NADH or NADPH, and assessing the presence and/or amount of the NAD+, NADP+, NADH or NADPH.

65. The method of embodiment 54, wherein the presence and/or amount of the aryl alcohol molecule or unsaturated aliphatic alcohol molecule is assessed by:
 a) oxidizing the aryl alcohol molecule or unsaturated aliphatic alcohol molecule with an aryl alcohol oxidase or an aliphatic alcohol oxidase in the presence of oxygen to produce aryl aldehyde molecule or unsaturated aliphatic aldehyde molecule and $H_2O_2$;
 b) reducing the aryl aldehyde molecule or unsaturated aliphatic aldehyde molecule with an aryl alcohol dehydrogenase or an alcohol dehydrogenase in the presence of NADH or NADPH to form a reaction cycle in which the reduced aryl alcohol molecule or unsaturated aliphatic alcohol molecule is oxidized by the aryl alcohol oxidase or an aliphatic alcohol oxidase in the presence of oxygen to produce additional aryl aldehyde molecule or unsaturated aliphatic aldehyde molecule and $H_2O_2$; and
 c) assessing the presence and/or amount of the $H_2O_2$, or the amount of NADH, NADPH, NAD+, or NADP+.

66. The method of embodiment 65, wherein the presence and/or amount of the $H_2O_2$ is assessed by contacting the $H_2O_2$ with a peroxidase, an antipyrine, a phenol, and/or an aniline analog.

67. The method of embodiment 54, wherein the hydrolytic enzyme substrate comprises at least a part of a β-glycosidase substrate molecule, and the hydrolytic enzyme is a β-glycosidase or beta-galactosidase.

68. The method of embodiment 67, wherein the step of assessing the presence and/or amount of the aryl alcohol molecule or unsaturated aliphatic alcohol molecule comprises oxidizing the aryl alcohol molecule or unsaturated aliphatic alcohol molecule with an oxidizing reagent.

69. The method of embodiment 67, wherein the presence and/or amount of the aryl alcohol molecule or unsaturated aliphatic alcohol molecule is assessed by oxidizing the aryl alcohol molecule or unsaturated aliphatic alcohol molecule with an aryl alcohol oxidase or an aliphatic alcohol oxidase in the presence of oxygen to produce oxidized aryl alcohol molecule or unsaturated aliphatic alcohol molecule and $H_2O_2$ and assessing the presence and/or amount of the $H_2O_2$.

70. The method of embodiment 69, wherein the presence and/or amount of the $H_2O_2$ is assessed by contacting the $H_2O_2$ with a peroxidase, 4-AA and/or an aniline analog.

71. The method of embodiment 67, wherein the presence and/or amount of the aryl alcohol molecule or unsaturated aliphatic alcohol molecule is assessed by oxidizing the aryl alcohol molecule or unsaturated aliphatic alcohol molecule with an aryl alcohol dehydrogenase or an alcohol dehydrogenase in the presence of $NAD^+$ or $NADP^+$ to produce NADH or NADPH, and assessing the presence and/or amount of the NAD+, NADP+, NADH or NADPH.

72. The method of embodiment 67, wherein the presence and/or amount of the aryl alcohol molecule or unsaturated aliphatic alcohol molecule is assessed by:
 a) oxidizing the aryl alcohol molecule or unsaturated aliphatic alcohol molecule with an aryl alcohol oxidase or an aliphatic alcohol oxidase in the presence of oxygen to produce oxidized aryl alcohol molecule or unsaturated aliphatic alcohol molecule and $H_2O_2$;
 b) reducing the oxidized aryl alcohol molecule or unsaturated aliphatic alcohol molecule with an aryl alcohol dehydrogenase or an alcohol dehydrogenase in the presence of NADH or NADPH to form a reaction cycle in which the reduced aryl alcohol molecule or unsaturated aliphatic alcohol molecule is oxidized by the aryl alcohol oxidase or an aliphatic alcohol oxidase in the presence of oxygen to produce additional oxidized aryl alcohol molecule or unsaturated aliphatic alcohol molecule and $H_2O_2$; and
 c) assessing the presence and/or amount of the $H_2O_2$.

73. The method of embodiment 72, wherein the presence and/or amount of the $H_2O_2$ is assessed by contacting the $H_2O_2$ with a peroxidase, a phenol, an antipyrine, and/or an aniline analog.

74. The method of embodiment 54, wherein the hydrolytic enzyme substrate comprises at least a part of an alkaline phosphatase substrate molecule, and the hydrolytic enzyme is an alkaline phosphatase.

75. The method of embodiment 74, wherein the step of assessing the presence and/or amount of the aryl alcohol molecule or unsaturated aliphatic alcohol molecule comprises oxidizing the aryl alcohol molecule or unsaturated aliphatic alcohol molecule with an oxidizing reagent.

76. The method of embodiment 74, wherein the presence and/or amount of the aryl alcohol molecule or unsaturated aliphatic alcohol molecule is assessed by oxidizing the aryl alcohol molecule or unsaturated aliphatic alcohol molecule with an aryl alcohol oxidase or an aliphatic alcohol oxidase in the presence of oxygen to produce oxidized aryl alcohol molecule or unsaturated aliphatic alcohol molecule and $H_2O_2$, and assessing the presence and/or amount of the $H_2O_2$.

77. The method of embodiment 76, wherein the presence and/or amount of the $H_2O_2$ is assessed by contacting the $H_2O_2$ with a peroxidase, a phenol, an antipyrine, and/or an aniline analog.

78. The method of embodiment 74, wherein the presence and/or amount of the aryl alcohol molecule or unsaturated aliphatic alcohol molecule is assessed by oxidizing the aryl alcohol molecule or unsaturated aliphatic alcohol molecule with an aryl alcohol dehydrogenase or an alcohol dehydrogenase in the presence of $NAD^+$ or $NADP^+$ to produce NADH or NADPH, and assessing the presence and/or amount of the NAD+, NADP+, NADH or NADPH.

79. The method of embodiment 74, wherein the presence and/or amount of the aryl alcohol molecule or unsaturated aliphatic alcohol molecule is assessed by a) oxidizing the aryl alcohol molecule or unsaturated aliphatic alcohol molecule with an aryl alcohol oxidase or an aliphatic alcohol oxidase in the presence of oxygen to produce oxidized aryl alcohol molecule or unsaturated aliphatic alcohol molecule and $H_2O_2$;

b) reducing the oxidized aryl alcohol molecule or unsaturated aliphatic alcohol molecule with an aryl alcohol dehydrogenase or an alcohol dehydrogenase in the presence of NADH or NADPH to form a reaction cycle in which the reduced aryl alcohol molecule or unsaturated aliphatic alcohol molecule is oxidized by the aryl alcohol oxidase or an aliphatic alcohol oxidase in the presence of oxygen to produce additional oxidized aryl alcohol molecule or unsaturated aliphatic alcohol molecule and $H_2O_2$; and c) assessing the presence and/or amount of the $H_2O_2$.

80. The method of embodiment 79, wherein the presence and/or amount of the $H_2O_2$ is assessed by contacting the $H_2O_2$ with a peroxidase, a phenol, an antipyrine, and/or an aniline analog.

81. The method of any of the embodiments 54-80, which is conducted as part of an assay, isolation and/or production of a target.

82. The method of embodiment 81, wherein the target is an inorganic molecule, an organic molecule and/or a complex thereof.

83. The method of embodiment 82, wherein the organic molecule is selected from the group consisting of an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

84. The method of embodiment 82, which is conducted as part of an immunoassay, protein sequencing, nucleic acid amplification, hybridization or sequencing.

85. The method of embodiment 84, wherein the method is used to monitor RNA or DNA sequencing.

86. The method of embodiment 85, wherein the hydrolytic enzyme is alkaline phosphatase.

The present invention is further illustrated by the following exemplary embodiments.

EXAMPLES

Example 1

Synthesis of Substrates

Suitable hydrolytic enzyme substrates for use in the compositions and methods of the invention can be made by conventional methods using known starting materials. Examples of such hydrolytic enzyme substrates include p-MOBG (p-methoxybenzyl galactose) and HDEGP, which can be made from the known galactosyl bromide in protected form (tetra-acetate) using silver (I) oxide in dichloromethane, followed by hydrolysis with methoxide in methanol to remove the acetate protecting groups.

Synthesis of
p-Methoxybenzyl-β-D-Galactopyranoside
(P-MOBG) (MW: 300.3)

1). p-Methoxybenzyl 2,3,4,6-Tetra-O-Acetyl-O-D-Galactopyranoside (p-MBAGP) (MW: 468.38)

To a solution of 2.64 g (6.42 mmol) of acetobromo-α-D-galactose and 1.38 mL (11.06 mmol) of p-methoxybenzyl alcohol in 20 mL of dichloromethane was added 1.5 g of molecular sieves)(4A°). After stirring for 20 min at room temperature, 1.5 g (6.48 mmol) of silver(I) oxide was added. The reaction mixture was stirred overnight at room temperature and then filtered and concentrated. Chromatography of the residue on silica gel yielded 1.0 g (80.64%) of the product as a colorless syrup. $^1$H NMR (500 MHz, CDCl$_3$): δ=7.22, 6.88 (2 d, 4H, phenyl), $C_{22}H_{28}O_{11}$: calculated 468.5. found 491.6 (M+$^{23}$Na).

2). p-Methoxybenzyl-β-D-Galactopyranoside
(P-MOBG) (MW: 300.3)

After 1.0 g (2.14 mmol) of P-methoxybenzyl 2,3,4,6-tetra-O-acetyl-β-D-galactopyranoside (p-MBAGP) was co-evaporated with anhydrous methanol (3×10 mL), 10 mL of anhydrous methanol and 1 mL of 0.5 M sodium methoxide were added. The reaction mixture was stirred for 1 hr at room temperature and then was neutralized to pH 7.0 by addition of 2 N HCl. After the solvents were removed by evaporation at 20° C. to 30° C., the residue was purified by silica gel chromatography eluted by ethyl acetate and then ethyl acetate/ethanol (5/1). Product: 0.4 g of white solid. Yield: 62.2%. $^1$H NMR (500 MHz, CDCl$_3$/CD$_3$OD=90/10): δ=7.2, 6.76 (2d, 4H, phenyl), 4.74, 4.46 (2d, 2H, CH$_2$-phenyl), 4.18 (D, 1H, J1, 2=7.6 Hz, 1-H), 3.70 (s, 3H, CH$_3$O—), 3.30-3.78 (m, 6H). $C_{14}H_{20}O_7$: Calculated 300.3. found 299.2 (M−1) and 323.2 (M+$^{23}$Na).

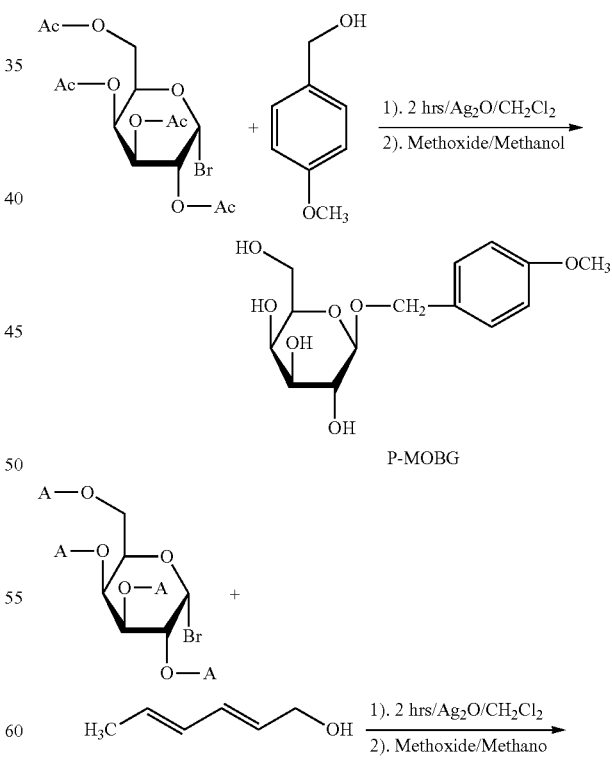

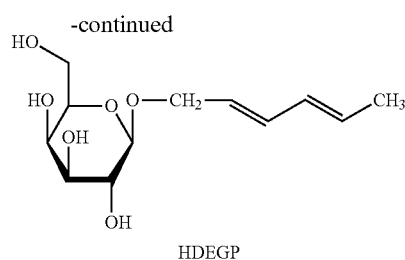

HDEGP

The substrate HDEG was synthesized by a similar procedures.

Example 2

Hydrolysis by Beta-Galactosidase

Hydrolytic enzyme substrates of the invention can be hydrolyzed by suitable enzymes matched with the substrate; thus PMOBG or HDEGP as shown above can be hydrolyzed by beta-galactosidase as illustrated below.

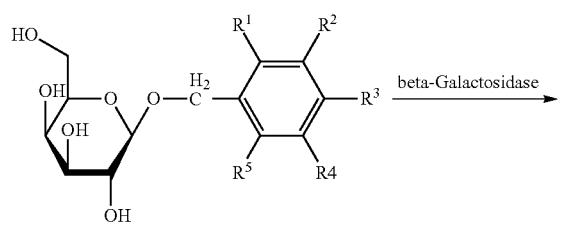

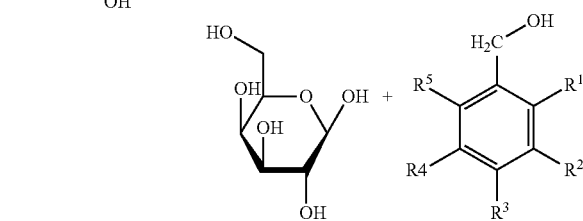

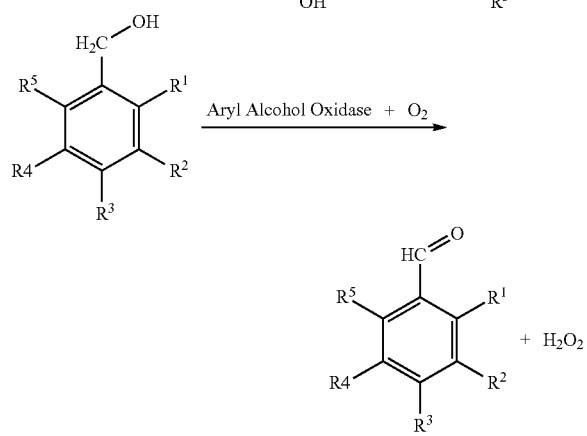

Incubation of 10 mM of p-MOBG with 10 unit/ml of beta-galactosidase and 20 unit/ml of aryl alcohol oxidase at 37° C. for 30 min resulted in generation of $H_2O_2$, which was detected by peroxidase in the presence of 4-AA and TOOS at 560 nm. When p-MOBG was incubated with aryl alcohol oxidase alone, there was no $H_2O_2$ detected, indicating p-MOBG is not a substrate for aryl alcohol oxidase but becomes the substrate for aryl alcohol oxidase only after hydrolysis of p-MOBG by beta-galactosidase. The aryl alcohol dehydrogenase used in this example was recombinantly produced based on the description in Guillen and Evans, *Appl. Environmental Microbiol.*, 60(8):2811-17 (1994) and Reiser et al., *J. Biol. Chem.*, 269(45):28152-28159 (1994).

Some specific examples of the hydrolysis reaction coupled with the enzymatic cycling reaction.

Example 3

| Reagent 1: | |
|---|---|
| Beta-galactosidase: | 50 unit/ml |
| Substrate p-MOBG: | 3 mM |
| Aryl alcohol oxidase: | 20 unit/ml |
| Aryl alcohol dehydrogenase: | 30 unit/ml |
| NADH: | 2 mM |
| Tris-HCl buffer, pH 9.0 | 50 mM |
| Reagent 2: | |
| Phosphate buffer, pH 6.3: | 100 mM |
| 4-AA: | 5 mM |
| Toos: | 5 mM |
| Horse radish peroxidase: | 10 unit/ml |

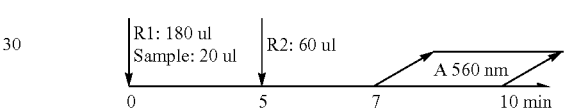

In this study, 180 μl of reagent 1 is mixed with 20 μl of a sample to be tested and the mixture is incubated at 37° C. for 5 minutes. Sixty (60) μl of reagent 2 is then added to the mixture and is incubated at 37° C. for another 5 minutes. The change of absorbance at 560 nm is measured for 2-5 minutes after the reagent 2 is added.

Example 4

| Reagent 1: | |
|---|---|
| Beta-galactosidase: | 30 unit/ml |
| Substrate HDEG: | 3 mM |
| Aryl alcohol oxidase: | 15 unit/ml |
| Alcohol dehydrogenase: | 40 unit/ml |
| NADPH: | 1 mM |
| Borate buffer, pH 9.1 | 30 mM |
| Reagent 2: | |
| Citric buffer, pH 6.0: | 100 mM |
| 4-AA: | 3 mM |
| Aniline analog: | 5 mM |
| Horse radish peroxidase: | 15 unit/ml |

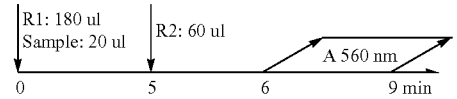

In this study, 180 μl of reagent 1 is mixed with 20 μl of a sample to be tested and the mixture is incubated at 37° C. for 5 minutes. Sixty (60) μl of reagent 2 is then added to the mixture and is incubated at 37° C. for another 4 minutes. The change of absorbance at 560 nm is measured for 1-4 minutes after the reagent 2 is added.

Example 5

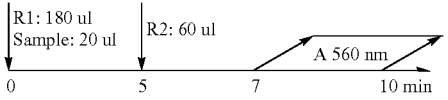

| Reagent 1: | |
|---|---|
| Alkaline phosphatase: | 50 unit/ml |
| Substrate AP: | 3 mM |
| Aryl alcohol oxidase: | 20 unit/ml |
| Aryl alcohol dehydrogenase: | 30 unit/ml |
| NADH: | 2 mM |
| Tris-HCl buffer, pH 9.0 | 50 mM |
| Reagent 2: | |
| Phosphate buffer, pH 6.3: | 100 mM |
| 4-AA: | 5 mM |
| Toos: | 5 mM |
| Horse radish peroxidase: | 10 unit/ml |

The structure of AP is shown in FIG. 4. In some examples, R1, R2, R4 and R5 are hydrogen, and R3 is —OCH3. In this study, 180 µl of reagent 1 is mixed with 20 µl of a sample to be tested and the mixture is incubated at 37° C. for 5 minutes. Sixty (60) µl of reagent 2 is then added to the mixture and is incubated at 37° C. for another 5 minutes. The change of absorbance at 560 nm is measured for 2-5 minutes after the reagent 2 is added.

Example 6

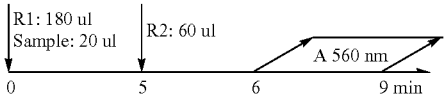

| Reagent 1: | |
|---|---|
| Acetylesterase: | 30 unit/ml |
| Substrate AE: | 3 mM |
| Aryl alcohol oxidase: | 15 unit/ml |
| Alcohol dehydrogenase: | 40 unit/ml |
| NADPH: | 1 mM |
| Borate buffer, pH 9.1 | 30 mM |
| Reagent 2: | |
| Citric buffer, pH 6.0: | 100 mM |
| 4-AA: | 3 mM |
| Aniline analog: | 5 mM |
| Horse radish peroxidase: | 15 unit/ml |

The structure of AE is shown in FIG. 5. In some examples, R1, R2, R4 and R5 are hydrogen, and R3 is —OCH3. In this study, 180 µl of reagent 1 is mixed with 20 µl of a sample to be tested and the mixture is incubated at 37° C. for 5 minutes. Sixty (60) µl of reagent 2 is then added to the mixture and is incubated at 37° C. for another 4 minutes. The change of absorbance at 560 nm is measured for 1-4 minutes after the reagent 2 is added.

Example 7

An exemplary AAO/AAD cycling system using an aryl alcohol oxidase (AAO) and an aryl alcohol dehydrogenase (AAD) was used to detect an aryl alcohol (see below).

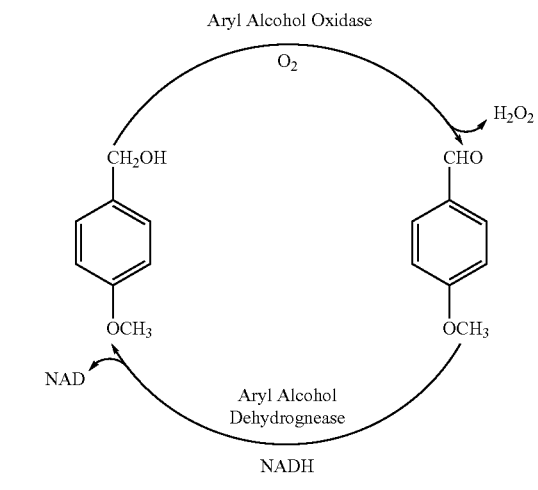

AAO was purified from *Pleurotus eryngii* using the procedures described in Guillen, F. et al., "Substrate specificity and properties of aryl-alcohol oxidase from the ligninolytic fungus *Pleurotus eryngii*," *Eur. J. Biochem.*, 209:603-611 (1992). The purification steps include concentration, anion exchange chromatography and hydrophobic interaction chromatography. DNA construct for recombinant production of *Pseudomonas putida* AAD was made based on the DNA sequence disclosed in Shaw, J. P. et al., Kinetic studies on benzyl alcohol dehydrogenase encoded by TOL plasmid pWW0," *J. Biol. Chem.*, 268:10842-10850 (1993), and the recombinant *Pseudomonas putida* AAD was made by overexpression in *E. coli*. The cycling system was combined with chemiluminescent (lumino)-hydrogen peroxide-horseradish peroxidase) reaction to form a sensitive assay.

For AAO, $K_{p-anisyl-OH}$=37±8 µM; and $k_{cat}$=117/s. For AAD, $K_{NADH}$=9.1±2 µM; $K_{p-Anisyl\ aldehyde}$=6.6±0.8 µM; and $k_{cat}$=30/s.

Reaction condition: Tris-HCL, pH 7, 100 mM; NADH 100 µM; EDTA 100 mM; HRP, 1.5 U; G6PH, 1 mM; G6PDH, 2 U; Luminol/enhancer, 5 µl; AAO, 20 µl (6 mg/ml); AAD, 20 µl (25 mg/ml) in a total volume 200 µl. AAD was added last to start the cycling reaction. The reaction was monitored for 10 minutes using impulse 2, CLIA reader from Monobind Inc.

Figure 10:
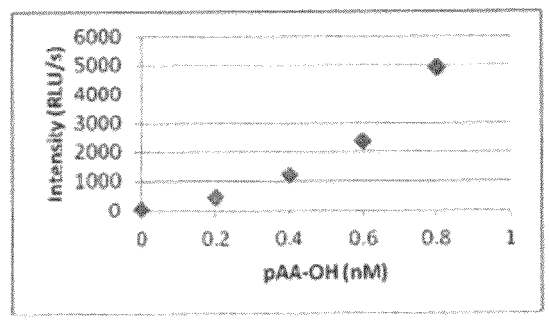
FIG. 10 illustrates detection of aryl alcohol with an exemplary AAO/AAD cycling system.

As shown in FIG. 10, the aryl alcohol can be detected as low as 0.2 nM with the AAO/AAD cycling system. Compared with the reaction only catalyzed by AAO, the detection limit for aryl alcohol with the AAO/AAD cycling system can be increased at least 1,000 fold higher.

Example 8

An exemplary AAO/AAD cycling system using an aryl alcohol oxidase (AAO) and an aryl alcohol dehydrogenase (AAD) as described in Example 7 was used to detect alkaline phosphatase (ALP).

Reaction condition: 50 µl ALP reaction system; Tris-HCl, pH 10.0 (100 mM); Anisyl phosphate (40 µM), 5 µl ALP reaction buffer. ALP reaction was kept for 5 mins.

200 µl cycling system: 50 µl ALP reaction system; AAO 10 µl (2.5 mg/ml); AAD 10 µl (20 mg/ml); NADH, 20 µM; G6PH, 2 mM; G6PDH, 2 U; HRP, 1.5 U; Hyperblue, 10 µl; and Tris-HCl, pH 7.0 (200 mM). AAD was added last to start the cycling reaction. The reaction was monitored for 30 minutes using impulse 2, CLIA reader from Monobind Inc.

Figure 11:
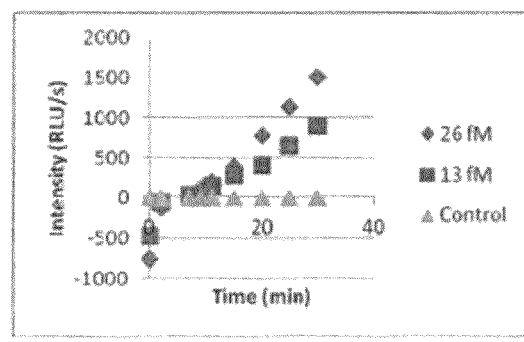
FIG. 11 illustrates detection of alkaline phosphatase with an exemplary AAO/AAD cycling system.

As shown in FIG. 11, when the assay was used to detect alkaline phosphatase in solution using 40 μM of anisyl phosphate as the substrate, 2.6 attomole of ALP can be detected. The detection sensitivity reached to sub attomole, and can be further improved with the optimization of ALP substrate concentration and increase of enzyme concentration and reaction time.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

The invention claimed is:

1. A method for assessing activity and/or amount of a hydrolytic enzyme in a sample, which method comprises:
   a) contacting a sample containing or suspected of containing a hydrolytic enzyme with a hydrolytic enzyme substrate having a structure of formula (I):

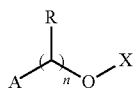
(I)

under conditions where said hydrolytic enzyme, if present in said sample, cleaves said substrate to produce an aryl alcohol molecule or unsaturated aliphatic alcohol molecule having a structure of formula (II) and a compound having a structure of formula (III):

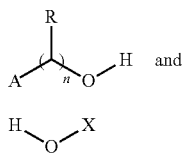
(II) and (III)

wherein
A is an aromatic or heteroaromatic group, a 1-alkene or a 1-alkyne, each of which is optionally substituted;
each R is independently H or an optionally substituted C1-C4 alkyl or aryl;
n is an integer from 1-4;
and X is a group comprising a substrate moiety; and
   b) assessing the presence and/or amount of said aryl alcohol molecule or unsaturated aliphatic alcohol molecule to assess activity and/or amount of said hydrolytic enzyme in said sample,
wherein the step of assessing the presence and/or amount of the aryl alcohol molecule or unsaturated aliphatic alcohol molecule comprises oxidizing the aryl alcohol molecule or unsaturated aliphatic alcohol molecule with enzymatic oxidation in the presence of oxygen to produce $H_2O_2$ and assessing the presence and/or amount of the $H_2O_2$, or enzymatic oxidation in the presence of $NAD^+$ or $NADP^+$ to produce NADH or NADPH, and assessing the presence and/or amount of the $NAD^+$, $NADP^+$, NADH or NADPH.

2. The method of claim 1, wherein the hydrolytic enzyme is an esterase, a beta-galactosidase, or a glycosidase.

3. The method of claim 1, wherein the step of assessing the presence and/or amount of the aryl alcohol molecule or unsaturated aliphatic alcohol molecule further comprises reducing a product of oxidizing the aryl alcohol molecule or unsaturated aliphatic alcohol molecule with a reducing reagent.

4. The method of claim 1, wherein the presence and/or amount of the aryl alcohol molecule or unsaturated aliphatic alcohol molecule is assessed by oxidizing the aryl alcohol molecule or unsaturated aliphatic alcohol molecule with an aryl alcohol oxidase or an aliphatic alcohol oxidase in the presence of oxygen to produce $H_2O_2$ and assessing the presence and/or amount of the $H_2O_2$.

5. The method of claim 1, wherein the presence and/or amount of the aryl alcohol molecule or unsaturated aliphatic alcohol molecule is assessed by oxidizing the aryl alcohol molecule or unsaturated aliphatic alcohol molecule with an aryl alcohol dehydrogenase or an alcohol dehydrogenase in the presence of $NAD^+$ or $NADP^+$ to produce NADH or NADPH, and assessing the presence and/or amount of the $NAD^+$, $NADP^+$, NADH or NADPH.

6. The method of claim 1, wherein the presence and/or amount of the aryl alcohol molecule or unsaturated aliphatic alcohol molecule is assessed by:
   a) oxidizing the aryl alcohol molecule or unsaturated aliphatic alcohol molecule with an aryl alcohol oxidase or an aliphatic alcohol oxidase in the presence of oxygen to produce aryl aldehyde molecule or unsaturated aliphatic aldehyde molecule and $H_2O_2$;
   b) reducing the aryl aldehyde molecule or unsaturated aliphatic aldehyde molecule with an aryl alcohol dehydrogenase or an alcohol dehydrogenase in the presence of NADH or NADPH to form a reaction cycle in which the reduced aryl alcohol molecule or unsaturated aliphatic alcohol molecule is oxidized by the aryl alcohol oxidase or an aliphatic alcohol oxidase in the presence of oxygen to produce additional aryl aldehyde molecule or unsaturated aliphatic aldehyde molecule and $H_2O_2$; and
   c) assessing the presence and/or amount of the $H_2O_2$, or the amount of NADH, NADPH, $NAD^+$, or $NADP^+$.

7. The method of claim 1, wherein the hydrolytic enzyme substrate comprises a substrate moiety of a β-glycosidase, and the hydrolytic enzyme is a β-glycosidase or beta-galactosidase.

8. The method of claim 7, wherein the step of assessing the presence and/or amount of the aryl alcohol molecule or unsaturated aliphatic alcohol molecule further comprises reducing a product of oxidizing the aryl alcohol molecule or unsaturated aliphatic alcohol molecule with a reducing reagent.

9. The method of claim 7, wherein the presence and/or amount of the aryl alcohol molecule or unsaturated aliphatic alcohol molecule is assessed by oxidizing the aryl alcohol molecule or unsaturated aliphatic alcohol molecule with an aryl alcohol oxidase or an aliphatic alcohol oxidase in the presence of oxygen to produce oxidized aryl alcohol molecule or unsaturated aliphatic alcohol molecule and $H_2O_2$ and assessing the presence and/or amount of the $H_2O_2$.

10. The method of claim 7, wherein the presence and/or amount of the aryl alcohol molecule or unsaturated aliphatic alcohol molecule is assessed by oxidizing the aryl alcohol molecule or unsaturated aliphatic alcohol molecule with an aryl alcohol dehydrogenase or an alcohol dehydrogenase in the presence of $NAD^+$ or $NADP^+$ to produce NADH or NADPH, and assessing the presence and/or amount of the $NAD^+$, $NADP^+$, NADH or NADPH.

11. The method of claim 7, wherein the presence and/or amount of the aryl alcohol molecule or unsaturated aliphatic alcohol molecule is assessed by:

a) oxidizing the aryl alcohol molecule or unsaturated aliphatic alcohol molecule with an aryl alcohol oxidase or an aliphatic alcohol oxidase in the presence of oxygen to produce oxidized aryl alcohol molecule or unsaturated aliphatic alcohol molecule and $H_2O_2$;
b) reducing the oxidized aryl alcohol molecule or unsaturated aliphatic alcohol molecule with an aryl alcohol dehydrogenase or an alcohol dehydrogenase in the presence of NADH or NADPH to form a reaction cycle in which the reduced aryl alcohol molecule or unsaturated aliphatic alcohol molecule is oxidized by the aryl alcohol oxidase or an aliphatic alcohol oxidase in the presence of oxygen to produce additional oxidized aryl alcohol molecule or unsaturated aliphatic alcohol molecule and $H_2O_2$; and
c) assessing the presence and/or amount of the $H_2O_2$.

12. The method of claim 7, wherein the hydrolytic enzyme is a β-glycosidase.

13. The method of claim 7, wherein the hydrolytic enzyme is a beta-galactosidase.

14. The method of claim 1, wherein the hydrolytic enzyme substrate comprises a substrate moiety of an alkaline phosphatase, and the hydrolytic enzyme is an alkaline phosphatase.

15. The method of claim 14, wherein the step of assessing the presence and/or amount of the aryl alcohol molecule or unsaturated aliphatic alcohol molecule further comprises reducing a product of oxidizing the aryl alcohol molecule or unsaturated aliphatic alcohol molecule with a reducing reagent.

16. The method of claim 14, wherein the presence and/or amount of the aryl alcohol molecule or unsaturated aliphatic alcohol molecule is assessed by oxidizing the aryl alcohol molecule or unsaturated aliphatic alcohol molecule with an aryl alcohol oxidase or an aliphatic alcohol oxidase in the presence of oxygen to produce oxidized aryl alcohol molecule or unsaturated aliphatic alcohol molecule and $H_2O_2$, and assessing the presence and/or amount of the $H_2O_2$.

17. The method of claim 14, wherein the presence and/or amount of the aryl alcohol molecule or unsaturated aliphatic alcohol molecule is assessed by oxidizing the aryl alcohol molecule or unsaturated aliphatic alcohol molecule with an aryl alcohol dehydrogenase or an alcohol dehydrogenase in the presence of $NAD^+$ or $NADP^+$ to produce NADH or NADPH, and assessing the presence and/or amount of the $NAD^+$, $NADP^+$, NADH or NADPH.

18. The method of claim 14, wherein the presence and/or amount of the aryl alcohol molecule or unsaturated aliphatic alcohol molecule is assessed by
a) oxidizing the aryl alcohol molecule or unsaturated aliphatic alcohol molecule with an aryl alcohol oxidase or an aliphatic alcohol oxidase in the presence of oxygen to produce oxidized aryl alcohol molecule or unsaturated aliphatic alcohol molecule and $H_2O_2$;
b) reducing the oxidized aryl alcohol molecule or unsaturated aliphatic alcohol molecule with an aryl alcohol dehydrogenase or an alcohol dehydrogenase in the presence of NADH or NADPH to form a reaction cycle in which the reduced aryl alcohol molecule or unsaturated aliphatic alcohol molecule is oxidized by the aryl alcohol oxidase or an aliphatic alcohol oxidase in the presence of oxygen to produce additional oxidized aryl alcohol molecule or unsaturated aliphatic alcohol molecule and $H_2O_2$; and
c) assessing the presence and/or amount of the $H_2O_2$.

19. The method of claim 1, which is conducted as part of an assay, isolation and/or production of a target.

20. The method of claim 19, which is conducted as part of an assay of a target.

21. The method of claim 19, which is conducted as part of isolation of a target.

22. The method of claim 19, which is conducted as part of production of a target.

23. The method of claim 1, which is conducted as part of an immunoassay, protein sequencing, nucleic acid amplification, hybridization or sequencing.

24. The method of claim 23, which is conducted as part of an immunoassay.

25. The method of claim 23, which is conducted as part of protein sequencing.

26. The method of claim 23, which is conducted as part of nucleic acid amplification.

27. The method of claim 23, which is conducted as part of nucleic acid hybridization.

28. The method of claim 23, which is conducted as part of nucleic acid sequencing.

29. The method of claim 1, wherein the step of assessing the presence and/or amount of the aryl alcohol molecule or unsaturated aliphatic alcohol molecule comprises oxidizing the aryl alcohol molecule or unsaturated aliphatic alcohol molecule with enzymatic oxidation in the presence of oxygen to produce $H_2O_2$ and assessing the presence and/or amount of the $H_2O_2$.

30. The method of claim 1, wherein the step of assessing the presence and/or amount of the aryl alcohol molecule or unsaturated aliphatic alcohol molecule comprises oxidizing the aryl alcohol molecule or unsaturated aliphatic alcohol molecule with enzymatic oxidation in the presence of $NAD^+$ to produce NADH, and assessing the presence and/or amount of the $NAD^+$ or NADH.

31. The method of claim 1, wherein the step of assessing the presence and/or amount of the aryl alcohol molecule or unsaturated aliphatic alcohol molecule comprises oxidizing the aryl alcohol molecule or unsaturated aliphatic alcohol molecule with enzymatic oxidation in the presence of $NADP^+$ to produce NADPH, and assessing the presence and/or amount of the $NADP^+$ or NADPH.

* * * * *